United States Patent
Kitahara et al.

(10) Patent No.: US 10,093,912 B2
(45) Date of Patent: Oct. 9, 2018

(54) NITRILE HYDRATASE

(71) Applicant: Mitsubishi Chemical Corporation, Tokyo (JP)

(72) Inventors: Aya Kitahara, Tokyo (JP); Takanori Akiyama, Kanagawa (JP); Miki Wakamatsu, Kanagawa (JP); Fumiaki Watanabe, Kanagawa (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 15/316,328

(22) PCT Filed: May 12, 2015

(86) PCT No.: PCT/JP2015/002396
§ 371 (c)(1),
(2) Date: Dec. 5, 2016

(87) PCT Pub. No.: WO2015/186298
PCT Pub. Date: Dec. 10, 2015

(65) Prior Publication Data
US 2017/0283784 A1   Oct. 5, 2017

(30) Foreign Application Priority Data
Jun. 6, 2014 (JP) .................. 2014-118041

(51) Int. Cl.
| C12N 9/88 | (2006.01) |
| C12P 13/02 | (2006.01) |
| C12P 21/06 | (2006.01) |
| C12P 19/34 | (2006.01) |
| C12N 15/00 | (2006.01) |
| C12N 1/20 | (2006.01) |
| C12N 1/00 | (2006.01) |
| C07H 21/04 | (2006.01) |
| C07K 1/00 | (2006.01) |

(52) U.S. Cl.
CPC .............. *C12N 9/88* (2013.01); *C12P 13/02* (2013.01); *C12Y 402/01084* (2013.01)

(58) Field of Classification Search
CPC .... C12N 9/88; C12Y 402/01084; C12P 13/02
USPC ....... 435/232, 129, 69.1, 91.1, 320.1, 252.3, 435/254.11; 536/23.1, 23.2; 530/350
See application file for complete search history.

(56) References Cited

U.S. PATENT DOCUMENTS

| 2007/0009985 A1 | 1/2007 | Yamaki et al. |
| 2007/0231868 A1 | 10/2007 | Watanabe et al. |
| 2008/0171389 A1 | 7/2008 | Verseck et al. |
| 2009/0162894 A1 | 6/2009 | Watanabe et al. |
| 2013/0035232 A1 | 2/2013 | Pierce et al. |
| 2014/0120588 A1 | 5/2014 | Watanabe et al. |
| 2014/0220644 A1 | 8/2014 | Watanabe et al. |
| 2015/0337287 A1 | 11/2015 | Watanabe et al. |
| 2016/0068833 A1 | 3/2016 | Watanabe et al. |
| 2016/0097046 A1 | 4/2016 | Watanabe et al. |

FOREIGN PATENT DOCUMENTS

| AU | 2004245849 B2 | 12/2004 |
| EP | 0 790 310 | 8/1997 |
| EP | 2 716 754 A1 | 4/2014 |
| EP | 2 719 760 A1 | 4/2014 |
| JP | 3162091 B2 | 4/2001 |
| JP | 2004-194588 A | 7/2004 |
| JP | 2005-160403 A | 6/2005 |
| JP | 2007-43910 A | 2/2007 |
| JP | 2007-143409 A | 6/2007 |
| JP | 2008-253182 A | 10/2008 |
| JP | 2010-172295 A | 8/2010 |
| RU | 2 081 173 C1 | 6/1997 |
| WO | WO 2004/056990 A1 | 7/2004 |
| WO | WO 2004/108942 A1 | 12/2004 |
| WO | WO 2005/090595 A2 | 9/2005 |
| WO | WO 2005/116206 A1 | 12/2005 |
| WO | WO 2009/009117 A2 | 1/2009 |
| WO | WO 2011/091374 A2 | 7/2011 |
| WO | WO 2012/164933 A1 | 12/2012 |

OTHER PUBLICATIONS

Kisselev L., Polypeptide release factors in prokaryotes and eukaryotes: same function, different structure. Structure, 2002, vol. 10: 8-9. (Year: 2002).*
Whisstock et al., Prediction of protein function from protein sequence. Q. Rev. Biophysics., 2003, vol. 36 (3): 307-340. (Year: 2003).*
Wishart et al., A single mutation converts a novel phosphotyrosine binding domain into a dual-specificity phosphatase. J. Biol. Chem., 1995, vol. 270(45): (Year: 1995).*
Witkowski et al., Conversion of b-ketoacyl synthase to a Malonyl Decarboxylase by replacement of the active cysteine with glutamine. Biochemistry, 1999, vol. 38: 11643-11650. (Year: 1999).*
Extended European Search Report dated May 15, 2017 in Patent Application No. 15803124.5.

(Continued)

*Primary Examiner* — Ganapathirama Raghu

(74) *Attorney, Agent, or Firm* — Oblon, McClelland, Maier & Neustadt, L.L.P.

(57) ABSTRACT

Provided is a novel improved nitrile hydratase with improved resistance to amide compounds under high temperatures. Specifically provided is a nitrile hydratase having at least one amino acid mutation selected from (a) to (d) below, in the amino acid sequence expressed in SEQ ID NO:50 ($X_1$ to $X_{27}$ represent independent arbitrarily-defined amino acid residuals). (a) $X_1$ is valine or glycine (b) $X_9$ is valine or threonine (c) $X_{23}$ is an amino acid selected from a group consisting of isoleucine, leucine, methionine and threonine, (d) $X_{24}$ is leucine.

13 Claims, 4 Drawing Sheets
Specification includes a Sequence Listing.

(56) References Cited

OTHER PUBLICATIONS

International Search Report dated Aug. 18, 2015 in PCT/JP2015/002396 (with English language translation).
Combine Russian Federation Office Action and Search Report dated Mar. 5, 2018 in Patent Application No. 2016152249/10(083692) (with English translation), 18 pages.
Office Action dated Apr. 4, 2018, in Australian patent application No. 2015270032 (7 pages).
Nitrile hydratase, alpha subunit [Pseudonocardia dioxanivorans CB1190]—GenBank, Accession AEA25435.1—Oct. 11, 2011—(2 pages).
Pseudonocardia dioxanivorans CB1190, complete genome—GenBank Accession CP002593.1—Oct. 11, 2011 —(1482 pages).
Nitrile hydratase, alpha subunit [Pseudonocardia dioxanivorans CB1190]—GenBank, Accession AEA26084.1—Oct. 11, 2011—(2 pages).
Nitrile hydratase, alpha subunit [Variovorax paradoxus EPS]—GenBank Accession AEA 36025.1 Dec. 31, 2013—1 page.
Nitrile hydratase alpha subunit [Variovorax boronicurnulans]—GenBank: Accession AER36563.1—Mar. 14, 2012 (1 page).
Nitrile hydratase subunit alpha [Streptomyces albulus]—GenBank: Accession AIA01551.1 Jun. 18, 2014 (1 page).
Nitrile hydratase, alpha subunit [Streptomyces iranensis] GenBank: Accession CDR13819.1 May 30, 2014 (1 page).

* cited by examiner

[Fig. 1]
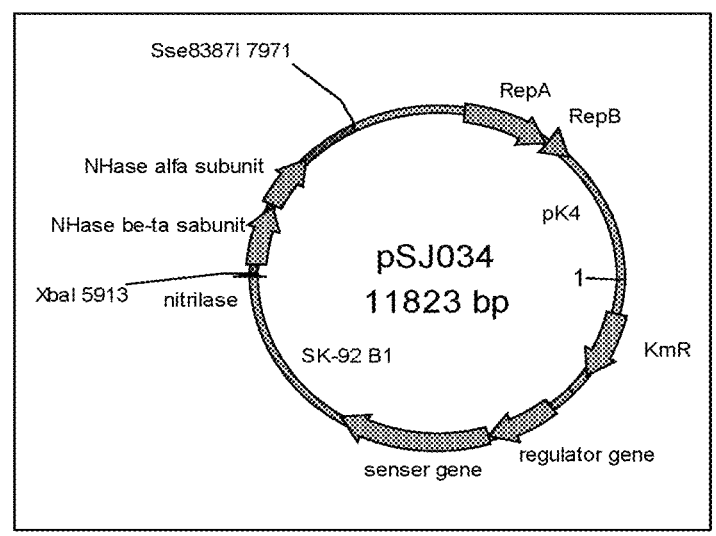

[Fig. 2-1]

```
Rhodococcus J1-H              1:------------------------MSEHVNKYTEYEARTKAIETLLYERGLITPAAVDRVVSYYENEIG  45
R. rhodocrous M8              1:------------------------MSEHVNKYTEYEARTKAIETLLYERGLITPAAVDRVVSYYENEIG  45
R. ruber TH                   1:------------------------MSEHVNKYTEYEARTKAIETLLYERGLITPAAVDRVVSYYENEIG  45
R. pyridinivorans_MW3         1:------------------------MSEHVNKYTEYEARTKAIETLLYERGLITPAAVDRVVSYYENEIG  45
R. pyridinivorans S85-2       1:------------------------MSEHVNKYTEYEARTKAIETLLYERGLITPAAVDRVVSYYENEIG  45
R. pyridinivorans MS-38       1:------------------------VSEHVNKYTEYEARTKAIETLLYERGLITPAAVDRVVSYYENEIG  45
Nocardia sp JBRs              1:------------------------MSEHVNKYTEYEARTKAIETLLYERGLITPAAVDRVVSYYENEIG  45
Nocardia YS-2002              1:------------------------MSEHVNKYTEYEARTKAIETLLYERGLITPAAVDRVVSYYENEIG  45
uncultured bacterium SP1      1:------------------------MSEHVNKYTEYEARTKAVETLLYERGLITPAAVDRVVSYYENEIG  45
uncultured bacterium BD2      1:------------------------MSEHVNKYTEYEARTKAIETLLYERGLITPAAVDRVVSYYENEIG  45
R. rhodocrous ATCC39484       1:------------------------VSEHVNKYTEYEARTKAIETLLYERGLITPAAVDRVVSYYENEIG  45
Sinorhizobium medicae WSM419  1:MSEHRHGPGEEHGHHHD-----NHLTDMEARVKALETVLTEKGLIDPAATDAIVDTYETKVG  57
G. thermoglucosidasius Q6     1:------------------------MSVQKVHHNVLPEKPAQTRTKALESLLTESGLVSTDALDALLEAYENDIG  50
P. thermophila JCM3095        1:------------------------MTENILRKSDEETQKETTARVKALESMLIEQGLLTTSMIDRMAELYENEVG  51
R. rhodocrous Cr4             1:------------------------MTAHNPVQGTFPRSNEELAARVKAMEAILVDKGLISTDALDYMSSVYENEVG  52
Comamonas testosteroni        1:---------MGQSHTHDHHHDGYQAPPEDIALRVKALESLLIEKGLVDPAAMDLVVQTYEHKVG  55
                                             .............*.**.*..*..*........*......**...*

Rhodococcus J1-H              46:PMGGAKVVAKSWVDPEYRKWLEEDATAAMASLGYAGEQAHQISAVFNDSQTHHVVVCTLC  105
R. rhodocrous M8              46:PMGGAKVVAKSWVDPEYRKWLEEDATAAMASLGYAGEQAHQISAVFNDSQTHHVVVCTLC  105
R. ruber TH                   46:PMGGAKVVAKSWVDPEYRKWLEEDATAAMASLGYAGEQAHQISAVFNDSQTHHVVVCTLC  105
R. pyridinivorans_MW3         46:PMGGAKVVAKSWVDPEYRKWLEEDATAAMASLGYAGEQAHQISAVFNDSQTHHVVVCTLC  105
R. pyridinivorans S85-2       46:PMGGAKVVAKSWVDPEYRKWLEEDATAAMASLGYAGEQAHQISAVFNDSQTHHVVVCTLC  105
R. pyridinivorans MS-38       46:PMGGAKVVAKSWVDPEYRKWLEEDATAAMASLGYAGEQAHQISAVFNDSQTHHVVVCTLC  105
Nocardia sp JBRs              46:PMGGAKVVAKSWVDPEYRKWLEEDATAAMASLGYAGEQAHQISAVFNDSQTHHVVVCTLC  105
Nocardia YS-2002              46:PMGGAKVVAKSWVDPEYRKWLEEDATAAMASLGYAGEQAHQISAVFNDSQTHHVVVCTLC  105
uncultured bacterium SP1      46:PMGGAKVVAKSWVDPEYRKWLEEDATAAMASLGYAGEQA-----------HHVVVCTLC  93
uncultured bacterium BD2      46:PMGGAKVVAKSWVDPEYRKWLEEDATAAMASLGYAGEQAHQISAVFNDSQTHHVVVCTLC  105
R. rhodocrous ATCC39484       46:PMGGAKVVAKSWVDPEYRKWLEEDATAAMASLGYAGEQAHQISAVFNDSQTHHVVVCTLC  105
Sinorhizobium medicae WSM419  58:PRNGARVVAKAWSDFDFADWLRRDATAATASLGFTGRQGEHMRAVFNTSETHNLIVCTLC  117
G. thermoglucosidasius Q6     51:PMNGAKVVAKPDPDYKERLLRDGTSAIAELGFLGLQGEHMVVVENTPKVHNVVVCTLC  110
P. thermophila JCM3095        52:PHLGAKVVVKAWTDPEFKKRLLADGTEACKELGIGGLQGEDMMWVENTDEVHHVVVCTLC  111
R. rhodocrous Cr4             53:PQLGAKIAAHAWVDPEFKQRLLADATGACKEMVGGMQGEEMVVLENTDTVNNMVVCTLC  112
Comamonas testosteroni        56:PRNGAKVVAKAWVDPAYKARLLADGTAGIAELGFSGVQGEDMVILENTPAVHNVVVCTLC  115
                                 *..**......*.**.....*..*.*........*..*.*...................*****

Rhodococcus J1-H              106:SCYPWPVLGLPPAWYKSMEYRSRVVADPRGVLKRDFGFDIPDEVEVRVWDSSSEIRYIVI  165
R. rhodocrous M8              106:SCYPWPVLGLPPAWYKSMEYRSRVVADPRGVLKRDFGFDIPDEVEVRVWDSSSEIRYIVI  165
R. ruber TH                   106:SCYPWPVLGLPPAWYKSMEYRSRVVADPRGVLKRDFGFDIPDEVEVRVWDSSSEIRYIVI  165
R. pyridinivorans_MW3         106:SCYPWPVLGLPPAWYKSMEYRSRVVADPRGVLKRDFGFDIPDEVEVRVWDSSSEIRYIVI  165
R. pyridinivorans S85-2       106:SCYPWPVLGLPPAWYKSMEYRSRVVADPRGVLKRDFGFDIPDEVEVRVWDSSSEIRYIVI  165
R. pyridinivorans MS-38       106:SCYPWPVLGLPPAWYKSMEYRSRVVADPRGVLKRDFGFDIPDEVEVRVWDSSSEIRYIVI  165
Nocardia sp JBRs              106:SCYPWPVLGLPPAWYKSMEYRSRVVADPRGVLKRDFGFDIPDEVEVRVWDSSSEIRYIVI  165
Nocardia YS-2002              106:SCYPWPVLGLPPAWYKSMEYRSRVVADPRGVLKRDFGFDIPDEVEVRVWDSSSEIRYIVI  165
uncultured bacterium SP1       94:SCYPWPVLGLPPAWYKSMEYRSRVVADPRGVLKRDFGFDIPDEVEVRVWDSSSEIRYIVI  153
uncultured bacterium BD2      106:SCYPWPVLGLPPAWYKSMEYRSRVVADPRGVLKRDFGFDIPDEVEVRVWDSSSEIRYIVI  165
R. rhodocrous ATCC39484       106:SCYPWPVLGLPPAWYKSMEYRSRVVADPRGVLKRDFGFDIPDEVEVRVWDSSSEIRYIVI  165
Sinorhizobium medicae WSM419  118:SCYPWAVLGLPPVWYKAPPYRSRAVIDPRGVL-AEFGLNLPAEKKIRVVDSTAELRYLVV  176
G. thermoglucosidasius Q6     111:SCYPWPVLGLPPVWYKSASYRARIVSEPRTVL-KEFGLELDDDVEIRVWDSSEIRYLVL  169
P. thermophila JCM3095        112:SCYPWPVLGLPNWFKEPQYRSRVVREPRQLLKEEFGFEVPPSKEIKVWDSSSEMRFVVL  171
R. rhodocrous Cr4             113:SCYPWPVLGLPNWYKPAYRARAARDPRGVM-AEFGYTPASDVEIRVWDSSAELRYWVL  171
Comamonas testosteroni        116:SCYPWPTLGLPPAWYKAPPYRSRMVSDPRGVL-AEFGLVTPA-KEIRVWDTTAELRYMVL  173
                                  *****..*****.*.*...**.*....**......**.........***...*.*..*.
```

[Fig. 2-2]

| | | | |
|---|---|---|---|
| Rhodococcus J1-H | 166:PERPAGTDGWSEEELTKLVSRDSMIGVSNALTPQEVIV | (SEQ ID NO: 4) | 203 |
| R. rhodocrous M8 | 166:PERPAGTDGWSEDELAKLVSRDSMIGVSNALTPQEVIV | (SEQ ID NO: 5) | 203 |
| R. ruber TH | 166:PERPAGTDGWSEDELAKLVSRDSMIGVSNALTPQEVIV | (SEQ ID NO: 6) | 203 |
| R. pyridinivorans_MW3 | 166:PERPAGTDGWSEEELTKLVSRDSMIGVSNALTPQEVIV | (SEQ ID NO: 7) | 203 |
| R. pyridinivorans S85-2 | 166:PERPAGTDGWSEEELTKLVSRDSMIGVSNALTPQEVIV | (SEQ ID NO: 8) | 203 |
| R. pyridinivorans MS-38 | 166:PERPAGTDGWSEEELTKLVSRDSMIGVSNALTPQEVIV | (SEQ ID NO: 9) | 203 |
| Nocardia sp JBRs | 166:PERPAGTDGWSEDELAKLVSRDSMIGVSNALTPQEVIV | (SEQ ID NO: 10) | 203 |
| Nocardia YS-2002 | 166:PERPAGTDGWSEDELAKLVSRDSMIGVSNALTPQEVIV | (SEQ ID NO: 11) | 203 |
| uncultured bacterium SP1 | 154:PERPAGTDGWSEEELTKLVSRDSIIGV------------------ | (SEQ ID NO: 12) | 180 |
| uncultured bacterium BD2 | 166:PERPAGTDGWSEEELTKLVSRDSMIGVSNALTPQEVIV | (SEQ ID NO: 13) | 203 |
| R. rhodocrous ATCC39484 | 166:PERPAGTDGWSEDELAKLVSRDSMIGVSNALTPQEVIV | (SEQ ID NO: 14) | 203 |
| Sinorhizobium medicae WSM419 | 177:PERPAATDDLGEDALAKLVTRDSMIGTGLALSPEAFR- | (SEQ ID NO: 15) | 213 |
| G. thermoglucosidasius Q6 | 170:PERPAGTEGWSEEELAKLVTRDSMIGVAKIKSPVKK--- | (SEQ ID NO: 16) | 205 |
| P. thermophila JCM3095 | 172:PQRPAGTDGWSEEEELATLVTRESMIGVEPAKAVA------ | (SEQ ID NO: 17) | 205 |
| R. rhodocrous Cr4 | 172:PQRPAGTENFTEEQLAALVTRDSLIGVSVPTAPNKA--- | (SEQ ID NO: 18) | 207 |
| Comamonas testosteroni | 174:PERPAGTEAYSEEQLAELVTRDSMIGTGLPIQPTTSH- | (SEQ ID NO: 19) | 210 |
| | *.***.*....*..*..**.*.*.**............ | | |

[Fig. 3]

MSEHVNK$X_1X_2X_3X_4X_5X_6$R$X_7$KA$X_8$ETLLYERGLITPAAVDRVVSYYENEIGPMG
GAKVVAKSWVDPEYRKWLEEDATAAMASLGYAGEQAHQI$X_9X_{10}X_{11}X_{12}$N$X_{13}X_{14}$
$X_{15}X_{16}X_{17}X_{18}X_{19}X_{20}X_{21}$C$X_{22}$LCSCYPWPVLGLPPAWYKSMEYRSRVVADPRGVL
KRDFGFDIPDEVEVR$X_{23}X_{24}$DS$X_{25}X_{26}$E$X_{27}$R$X_{28}X_{29}$VIPERPAGTDGWSEEELT
KLVSRDSMIGVSNALTPQEVIV (SEQ ID NO: 50)

NITRILE HYDRATASE

TECHNICAL FIELD

The present invention relates to an improved (mutated) nitrile hydratase and a method for producing the improved nitrile hydratase. Moreover, the present invention relates to DNA that encodes the enzyme, a recombinant vector containing the DNA, a transformant containing the recombinant vector, and a method for producing an amide compound.

BACKGROUND ART

A nitrile hydratase is an enzyme having nitrile hydration activity that catalyses the hydration of a nitrile group to an amide group. Also, corresponding amide compounds can be produced from nitrile compounds by using the enzyme or a microbial cell or the like containing the enzyme. Compared with conventional chemical synthetic methods, this method is known to have high conversion rate and high selectivity rate from a nitrile compound to a corresponding amide compound.

Examples of microorganisms that produce a nitrile hydratase include the genus *Corynebacterium*, genus *Pseudomonas*, genus *Rhodococcus*, genus *Rhizobium*, genus *Klebsiella*, genus *Pseudonocardia* and the like. Among those, *Rhodococcus rhodochrous* J1 strain has been used for industrial production of acrylamides, and its usefulness has been verified. Furthermore, a gene encoding a nitrile hydratase produced by the strain has been identified (see Patent Publication 1).

Meanwhile, introducing a mutation into a nitrile hydratase has been attempted not only to use a nitrile hydratase isolated from a naturally existing microorganism or its gene, but also to change its activity, substrate specificity, Vmax, Km, heat stability, stability against a substrate, stability against a subsequent product and the like of a nitrile hydratase. Regarding the nitrile hydratase in *Pseudonocardia thermophila* JCM 3095, from its three dimensional structure data, presumed sites relating to the substrate specificity or thermal stability are obtained, and mutant enzymes with modified substrate specificity were obtained among them (see Patent Publications 2 to 4). Also, nitrile hydratase genes with improved heat resistance and amide-compound resistance have been produced by the inventors of the invention (see Patent Publications 5 to 9).

However, developing a nitrile hydratase which has further enhanced heat resistance and resistance to amide compounds and can react at high temperatures and using the nitrile hydratase for production of an amide compound are very useful from the viewpoint of production cost like cost involved with catalyst, and obtaining enzymes with such performance is especially desired so as to achieve a reduction in the enzyme amount for reactions and in production costs or the like.

CITATION LIST

Patent Publication

Patent Publication 1: JP 3162091 B
Patent Publication 2: WO 2004/056990 A
Patent Publication 3: JP 2004-194588 A
Patent Publication 4: JP 2005-16403 A
Patent Publication 5: WO 2005/116206 A
Patent Publication 6: JP 2007-143409 A
Patent Publication 7: JP 2007-43910 A
Patent Literature 8: JP 2008-253182 A
Patent Literature 9: JP 2010-172295 A

SUMMARY OF THE INVENTION

Problems to be Solved by the Invention

The objective of the invention is to have a method for producing an amide compound with higher production efficiency by providing a novel improved nitrile hydratase with enhanced resistance to amide compounds under high temperatures.

Means for Solving Problem

To solve the problems described above, inventors of the invention conducted intensive studies, and as a result, found that a protein in which a specific amino acid residue in the amino sequence of a nitrile hydratase is substituted with another amino acid residue has a nitrile hydratase activity and exhibits enhanced resistance to amide compounds under high temperatures. The invention is completed accordingly.

Namely, the invention provides the following [1] to [13].

[1] An improved nitrile hydratase having at least one amino acid sequence represented by the following SEQ ID NO: 46 to 49 in the α subunit;
(a) SEQ ID NO: 46: $X_1X_2X_3X_4X_5X_6RX_7KAX_8E$
(with the proviso that, R indicates arginine, K indicates lysine, A indicates alanine, E indicates glutamic acid, $X_1$ indicates an amino acid other than tyrosine, and $X_2$ to $X_8$ each independently indicate any amino acid residue);
(b) SEQ ID NO: 47: $X_9X_{10}X_{11}X_{12}NX_{13}X_{14}X_{15}X_{16}X_{17}X_{18}X_{19}X_{20}X_{21}CX_{22}LC$
(with the proviso that, N indicates asparagine, V indicates valine, C indicates cysteine, T indicates threonine, L indicates leucine, $X_9$ indicates an amino acid other than serine, and $X_{10}$ to $X_{22}$ each independently indicate any amino acid residue);
(c) SEQ ID NO: 48: $X_{23}WDSX_{25}X_{26}EX_{27}RX_{28}X_{29}V$
(with the proviso that, W indicates tryptophane, D indicates asparaginic acid, S indicates serine, E indicates glutamic acid, R indicates arginine, V indicates valine, $X_{23}$ indicates an amino acid other than valine, and $X_{25}$ to $X_{29}$ each independently indicate any amino acid residue);
(d) SEQ ID NO: 49: $VX_{24}DSX_{25}X_{26}EX_{27}RX_{28}X_{29}V$
(with the proviso that, V indicates valine, D indicates asparaginic acid, S indicates serine, E indicates glutamic acid, R indicates arginine, $X_{24}$ indicates an amino acid other than tryptophane, and $X_{25}$ to $X_{29}$ each independently indicate any amino acid residue);
[2] The improved nitrile hydratase described in above [1], in which the improved nitrile hydratase has at least one amino acid sequence represented by the following SEQ ID NO: 46 to 49 in the α subunit;
(a) SEQ ID NO: 46: $X_1X_2X_3X_4X_5X_6RX_7KAX_8E$
(with the proviso that, R indicates arginine, K indicates lysine, A indicates alanine, E indicates glutamic acid, $X_1$ indicates an amino acid other than tyrosine, and $X_2$ to $X_8$ each independently indicate any amino acid residue);
(b) SEQ ID NO: 47: $X_9X_{10}X_{11}X_{12}NX_{13}X_{14}X_{15}X_{16}X_{17}X_{18}X_{19}X_{20}X_{21}CX_{22}LC$
(with the proviso that, N indicates asparagine, V indicates valine, C indicates cysteine, T indicates threonine, L indicates leucine, $X_9$ indicates an amino acid other than serine, $X_{10}$ to $X_{20}$ each independently indicate any amino acid residue, $X_{21}$ indicates valine, and $X_{22}$ indicates threonine);

(c) SEQ ID NO: 48: $X_{23}WDSX_{25}X_{26}EX_{27}RX_{28}X_{29}V$
(with the proviso that, W indicates tryptophane, D indicates asparaginic acid, S indicates serine, E indicates glutamic acid, R indicates arginine, V indicates valine, $X_{23}$ indicates an amino acid other than valine, and $X_{25}$ to $X_{29}$ each independently indicate any amino acid residue);

(d) SEQ ID NO: 49: $VX_{24}DSX_{25}X_{26}EX_{27}RX_{28}X_{29}V$
(with the proviso that, V indicates valine, D indicates asparaginic acid, S indicates serine, E indicates glutamic acid, R indicates arginine, $X_{24}$ indicates an amino acid other than tryptophane, and $X_{25}$ to $X_{29}$ each independently indicate any amino acid residue);

[3] The improved nitrile hydratase described in above [1], in which the improved nitrile hydratase has at least one amino acid sequence represented by the following SEQ ID NO: 46 to 49 in the α subunit;

(a) SEQ ID NO: 46: $X_1X_2X_3X_4X_5X_6RX_7KAX_8E$
(with the proviso that, R indicates arginine, K indicates lysine, A indicates alanine, E indicates glutamic acid, $X_1$ indicates glycine or valine, and $X_2$ to $X_8$ each independently indicate any amino acid residue);

(b) SEQ ID NO: 47: $X_9X_{10}X_{11}X_{12}NX_{13}X_{14}X_{15}X_{16}X_{17}X_{18}X_{19}X_{20}X_{21}CX_{22}LC$
(with the proviso that, N indicates asparagine, V indicates valine, C indicates cysteine, T indicates threonine, L indicates leucine, $X_9$ indicates valine or threonine, $X_{10}$ to $X_{20}$ each independently indicate any amino acid residue, $X_{21}$ indicates valine, and $X_{22}$ indicates threonine);

(c) SEQ ID NO: 48: $X_{23}WDSX_{25}X_{26}EX_{27}RX_{28}X_{29}V$
(with the proviso that, W indicates tryptophane, D indicates asparaginic acid, S indicates serine, E indicates glutamic acid, R indicates arginine, V indicates valine, $X_{23}$ is selected from a group consisting of isoleucine, leucine, methionine and threonine, and $X_{25}$ to $X_{29}$ each independently indicate any amino acid residue);

(d) SEQ ID NO: 49: $VX_{24}DSX_{25}X_{26}EX_{27}RX_{28}X_{29}V$
(with the proviso that, V indicates valine, D indicates asparaginic acid, S indicates serine, E indicates glutamic acid, R indicates arginine, $X_{24}$ indicates leucine, and $X_{25}$ to $X_{29}$ each independently indicate any amino acid residue);

[4] The improved nitrile hydratase described in any one of above [1] to [3], in which in the above SEQ ID NO: 46, $X_2$ indicates T (threonine), $X_3$ indicates E (glutamic acid), $X_4$ indicates Y (tyrosine), $X_5$ indicates E (glutamic acid), $X_6$ indicates A (alanine), $X_7$ indicates T (threonine), and $X_8$ indicates I (isoleucine),
in the above SEQ ID NO: 47, $X_{10}$ indicates A (alanine), $X_{11}$ indicates V (valine), $X_{12}$ indicates F (phenylalanine), $X_{13}$ indicates D (asparaginic acid), $X_{14}$ indicates S (serine), $X_{15}$ indicates Q (glutamine), $X_{16}$ indicates T (threonine), $X_{17}$ indicates H (histidine), $X_{18}$ indicates H (histidine), $X_{19}$ indicates V (valine) and $X_{20}$ indicates V (valine), and
in the above SEQ ID NO: 48 and 49, $X_{25}$ indicates S (serine), $X_{26}$ indicates S (serine), $X_{27}$ indicates I (isoleucine), $X_{28}$ indicates Y (tyrosine) and $X_{29}$ indicates I (isoleucine); and
the amino acid sequence represented by SEQ ID NO: 46 corresponds to positions 8 to 19 of the amino acid sequence of the α subunit of a nitrile hydratase, the amino acid sequence represented by SEQ ID NO: 47 corresponds to positions 88 to 105 of the same sequence, and the amino acid sequence represented by SEQ ID NO: 48 and 49 corresponds to positions 153 to 164 of the same sequence;

[5] The improved nitrile hydratase described in any one of above [1] to [4], in which the improved nitrile hydratase has an amino sequence represented by SEQ ID NO: 50;

[6] An improved nitrile hydratase having an amino acid sequence represented by SEQ ID NO: 50 in the α subunit, in which at least one amino acid mutation selected from the following (i) to (iv) is included:
(i) $X_1$ indicates G (glycine) or V (valine),
(ii) $X_9$ indicates V (valine) or T (threonine),
(iii) $X_{23}$ is an amino acid selected from a group consisting of I (isoleucine), L (leucine), M (methionine) and T (threonine), and
(iv) $X_{24}$ indicates L (leucine);

[7] The improved nitrile hydratase described in above [6], in which the $X_2$ indicates T (threonine), $X_3$ indicates E (glutamic acid), $X_4$ indicates Y (tyrosine), $X_5$ indicates E (glutamic acid), $X_6$ indicates A (alanine), $X_7$ indicates T (threonine), $X_8$ indicates I (isoleucine), $X_{10}$ indicates A (alanine), $X_{11}$ indicates V (valine), $X_{12}$ indicates F (phenylalanine), $X_{13}$ indicates D (asparaginic acid), $X_{14}$ indicates S (serine), $X_{15}$ indicates Q (glutamine), $X_{16}$ indicates T (threonine), $X_{17}$ indicates H (histidine), $X_{18}$ indicates H (histidine), $X_{19}$ indicates V (valine), $X_{20}$ indicates V (valine), $X_{25}$ indicates S (serine), $X_{26}$ indicates S (serine), $X_{27}$ indicates I (isoleucine), $X_{28}$ indicates Y (tyrosine) and $X_{29}$ indicates I (isoleucine);

[8] The improved nitrile hydratase described in any one of above [1] to [7], in which the nitrile hydratase is derived from *Rhodococcus* bacterium or *Nocardia* bacterium;

[9] DNA encoding the improved nitrile hydratase described in any one of above [1] to [8], or DNA which hybridizes under stringent conditions with the DNA having a base sequence complementary to the above-mentioned DNA and encodes a protein having nitrile hydratase activity with enhanced resistance to amide compounds under high temperatures;

[10] A recombinant vector containing the DNA described in above [9];

[11] A transformant containing the recombinant vector described in above [10];

[12] A method for producing a nitrile hydratase, the method including culturing the transformant described in above [11] and collecting the nitrile hydratase from the obtained culture; and

[13] A method for producing an amide compound, the method including bringing a nitrile compound into contact with the improved nitrile hydratase described in any one of above [1] to [8], or with a culture which is obtained by culturing the transformant described in above [11] or a processed product of the culture.

Effect of the Invention

According to the invention, a novel improved (mutated) nitrile hydratase with enhanced resistance to amide compounds under high temperatures can be provided. The improved nitrile hydratase of the invention has excellent resistance to amide compounds under high temperatures and allows improvement of efficiency for producing amide compounds.

BRIEF DESCRIPTION OF DRAWINGS

FIG. 1 is a schematic view illustrating plasmid pSJ034;
FIG. 2-1 is a drawing illustrating the amino acid sequence (part of N-terminal side) of the α subunit of nitrile hydratase derived from various microorganisms.

FIG. 2-2 is a drawing illustrating the same amino acid sequences as FIG. 2-1, and it shows the sequences subsequent to the amino acid sequences of FIG. 2-1.

FIG. 3 illustrates the amino acid sequence of the α subunit of the invention which is represented by SEQ ID NO: 50.

The present application claims the benefit of priority to Japanese Patent Application No. 2014-118041 (filed on Jun. 6, 2014) and the disclosure of which is incorporated herein by reference in its entirety.

MODE(S) FOR CARRYING OUT THE INVENTION

1. Nitrile Hydratase
1.1 Known Nitrile Hydratase

A "nitrile hydratase" has a high dimensional structure which consists of a group of α and β subunit domains, and contains a non-heme iron atom or a non-corrin cobalt atom as a prosthetic molecule. Those nitrile hydratases are identified and referred to as an iron-containing nitrile hydratase and a cobalt-containing nitrile hydratase, respectively.

A representative example of the iron-containing nitrile hydratase includes a hydratase derived from Rhodococcus N-771 strain. The three dimensional structure of such an iron-containing nitrile hydratase has been clearly identified by X-ray crystal structural analysis. The enzyme is bonded with non-heme iron via four amino acid residues in a cysteine cluster (Cys-Ser-Leu-Cys-Ser-Cys) (SEQ ID NO: 56) forming the active site of the α subunit As for the cobalt-containing nitrile hydratase, examples are those derived from *Rhodococcus rhodochrous* J1 strain (hereinafter may be referred to as "J1 strain") or derived from *Pseudonocardia thermophila*.

A cobalt-containing nitrile hydratase derived from the J1 strain is bound with a cobalt atom via a region identified as a cysteine cluster (Cys-Thr-Leu-Cys-Ser-Cys) (SEQ ID NO: 57 that forms the active site of the α subunit. In the cysteine cluster of a cobalt-containing nitrile hydratase derived from Pseudonocardia thermophila, cysteine (Cys) at position 4 from the upstream side (N-terminal side) of the cysteine cluster derived from the J1 strain is cysteine sulfinic acid (Csi), and cysteine (Cys) at position 6 from the furthermost downstream side (C-terminal side) of the cysteine cluster derived from the J1 strain is cysteine sulfenic acid (Cse).

As described above, a prosthetic molecule is bonded with a region identified as cysteine clusters "C(S/T)LCSC" (SEO ID NO: 55) in the α subunit. Examples of a nitrile hydratase containing a binding region with such a prosthetic molecule are those that have amino acid sequences and are encoded by gene sequences derived from the following: *Rhodococcus rhodochrous* J1 (FERM BP-1478), *Rhodococcus rhodochrous* M8 (Old Soviet Union Patent No. 1731814 (SU 1731814), *Rhodococcus rhodochrous* M33 (VKM Ac-1515D), *Rhodococcus rhodochrous* ATCC 39484 (JP 2001- 292772 A), *Bacillus smithii* (JP 9-248188 A), *Pseudonocardia thermophila* (JP 9- 275978 A) or *Geobacillus thermoglucosidasius*. On the other hand, the β subunit is thought to be attributed to structural stability.

The nitrile hydratase derived from *Rhodococcus rhodochrous* J1 strain (FERM BP-1478) has the GenBank accession number of "P21220". Furthermore, the GenBank accession number of the α subunit derived from *Rhodococcus rhodochrous* M8 (SU 1731814) is "ATT79340" and the GenBank accession number of the β subunit is "AAT 79339." The GenBank accession number of the nitrile hydratase gene derived from *Rhodococcus pyridinivorans* MW3 is "AJ582605," and the GenBank accession number of the nitrile hydratase gene derived from *Rhodococcus pyridinivorans* S85-2 is "AJ582605." The nitrile hydratase gene of *Rhodococcus ruber* RH (CGMCC No. 2380) is described in Chinese Patent No. 101463358 (CN1463358). Moreover, the GenBank accession number of the nitrile hydratase gene derived from *Nocardia* YS-2002 is "X86737," and the GenBank accession number of the nitrile hydratase gene derived from *Nocardia* sp. JBRs is "AY141130."

In SEQ ID NOs: 1 to 19 of Sequence Listing, amino acid sequence and base sequence of known nitrile hydratase are described.

SEQ ID NO: 1: base sequence of the β subunit derived from *Rhodococcus rhodochrous* J1

SEQ ID NO: 2: amino sequence of the β subunit derived from *Rhodococcus rhodochrous* J1

SEQ ID NO: 3: base sequence of the α subunit derived from *Rhodococcus rhodochrous* J1

SEQ ID NO: 4: amino sequence of the α subunit derived from *Rhodococcus rhodochrous* J1

SEQ ID NO: 5: amino sequence of the α subunit of *Rhodococcus rhodochrous* M8

SEQ ID NO: 6: amino sequence of the α subunit of *Rhodococcus ruber* TH

SEQ ID NO: 7: amino sequence of the α subunit of *Rhodococcus pyridinivorans* MW33

SEQ ID NO: 8: amino sequence of the α subunit of *Rhodococcus pyridinivorans* S85-2

SEQ ID NO: 9: amino sequence of the α subunit of *Rhodococcus pyridinivorans* MS-38

SEQ ID NO: 10: amino sequence of the α subunit of *Nocardia* sp. JBRs

SEQ ID NO: 11: amino sequence of the α subunit of *Nocardia* sp. YS-2002

SEQ ID NO: 12: amino sequence of the α subunit of Uncultured bacterium SP1

SEQ ID NO: 13: amino sequence of the α subunit of Uncultured bacterium BD2

SEQ ID NO: 14: amino sequence of the α subunit of *Rhodococcus rhodochrous* ATCC39484

SEQ ID NO: 15: amino sequence of the α subunit of *Sinorhizobium medicae* WSM419

SEQ ID NO: 16: amino sequence of the α subunit of *Sinorhizobium medicae* Q6

SEQ ID NO: 17: amino sequence of the α subunit of *Pseudonocardia thermophila* JCM3095

SEQ ID NO: 18: amino sequence of the α subunit of *Rhodococcus rhodochrous* Cr4

SEQ ID NO: 19: amino sequence of the α subunit of *Comamonas testosterone*.

Furthermore, FIG. 2-1 and FIG. 2-2 show the alignments of amino acid sequences (in one-letter code) in the α subunits of known nitrile hydratase derived from various microorganisms. In each of FIG. 2-1 and FIG. 2-2, each amino acid sequence corresponds to SEQ ID NO: 4, 5 to 19 in the order from the top.

The nitrile hydratase according to the invention is not limited to one with the above sequence, but includes a protein having an amino acid sequence that is homologous or identical to the amino acid sequence described in any one of SEQ ID NOs: 1 to 19 at approximately 60% or higher, preferably at approximately 70% or higher, more preferably at approximately 80% or higher, even more preferably at approximately 90% or higher, particularly preferably at approximately 95% or higher, and most preferably at approximately 98% or higher, while also possessing the nitrile hydratase activity.

In addition, regarding the nitrile hydratase of the invention, a protein which has the amino acid sequence described in any one of SEQ ID NOs: 1 to 19 in which 1 to several amino acids, specifically, 1 to 20, preferably 1 to 10, more preferably 1 to 5, and even more preferably 1 to 2 amino acids are deleted, substituted, or added, and also has the nitrile hydratase activity is also included in the nitrile hydratase of the invention.

1.2 Improved Nitrile Hydratase

The improved nitrile hydratase of the invention is a novel improved nitrile hydratase with enhanced resistance to amide compounds under high temperatures.

The improved nitrile hydratase of the invention is not limited to being derived from any specific type. For example, those registered as nitrile hydratase in the GenBank database Hypertext Transfer Protocol://World Wide Web.ncbi.nlm.nih.gov/entrez/query.fcgi?CMD=search&DB=protein provided by the U.S. National Center for Biotechnology Information (NCBI), or those described as nitrile hydratase in publications, may be referred to for a use.

Specific examples include nitrile hydratases that are described in WO 2005/116206 A, JP 2007-143409 A, JP 2007-43910 A, JP 2008-253182 A, or JP 2010-172295 A (incorporated in the present specification by reference). Those nitrile hydratases have heat resistance or resistance of acrylamide. By further adding an amino acid substitution according to the invention, a property for enhancing the resistance to amide compounds under high temperatures can be obtained.

Examples of the improved nitrile hydratase of the invention include a nitrile hydratase of which α subunit has the amino acid sequence (SEQ ID NO: 50) shown in FIG. 3. Among the amino acid sequences shown in FIG. 3, there are the amino acid sequence represented by SEQ ID NO: 46 on $8^{th}$ to $19^{th}$ amino acids when counted from the N terminal, the amino acid sequence represented by SEQ ID NO: 47 on $88^{th}$ to $105^{th}$ amino acids, and the amino acid sequence represented by SEQ ID NO: 48 or SEQ ID NO: 49 on $153^{rd}$ to $165^{th}$ amino acids.

Regarding the amino acid sequence represented by SEQ ID NO: 50, one having at least one amino acid mutation selected from (a) to (d) can be mentioned as one embodiment of the invention ($X_1$ to $X_{29}$ represent an independent arbitrary amino acid residue).

(a) $X_1$ is glycine or valine
(b) $X_9$ is valine or threonine
(c) $X_{23}$ is an amino acid selected from a group consisting of isoleucine, leucine, methionine, and threonine
(d) $X_{24}$ is leucine As another embodiment, an improved nitrile hydratase having the amino acid sequence represented by SEQ ID NO: 50 in which $X_2$ is T (threonine), $X_3$ is E (glutamic acid), $X_4$ is Y (tyrosine), $X_5$ is E (glutamic acid), $X_6$ is A (alanine), $X_7$ is T (threonine), $X_8$ is I (isoleucine), $X_{10}$ is A (alanine), $X_{11}$ is V (valine), $X_{12}$ is F (phenylalanine), $X_{13}$ is D (asparaginic acid), $X_{14}$ is S (serine), $X_{15}$ is Q (glutamine), $X_{16}$ is T (threonine), $X_{17}$ is H (histidine), $X_{18}$ is H (histidine), $X_{19}$ is V (valine), $X_{20}$ is V (valine), $X_{25}$ is S (serine), $X_{26}$ is S (serine), $X_{27}$ is I (isoleucine), $X_{28}$ is Y (tyrosine), $X_{29}$ is I (isoleucine) and also has at least one characteristic selected from the above (a) to (d) can be mentioned.

Meanwhile, also included in the improved nitrile hydratase of the invention is a nitrile hydratase that is homologous or identical to, at a position other than the aforementioned substitution portions, the amino acid sequence described in SEQ ID NO: 50 at approximately 70% or higher, preferably at approximately 80% or higher, more preferably at approximately 90% or higher, even more preferably at approximately 95% or higher, and particularly preferably at approximately 98% or higher, while also possessing the same heat resistance and/or resistance to amide compounds.

Also included in the improved nitrile hydratase of the invention is a nitrile hydratase which has the amino acid sequence described in SEQ ID NO: 50 in which 1 to 10, preferably 1 to 5, and more preferably 1 to 2 amino acids are deleted, substituted, or added at a position other than the aforementioned substitution portions and has the same heat resistance and/or resistance to amide compounds.

As another example of the improved nitrile hydratase of the invention, regarding the amino acid sequence represented by SEQ ID NO: 4 of a known nitrile hydratase, one having at least one characteristic selected from (e) to (h) can be mentioned.

(e) the $8^{th}$ amino acid residue (tyrosine) of the α subunit is substituted with glycine or valine
(f) the $88^{th}$ amino acid residue (serine) of the α subunit is substituted with valine or threonine
(g) the $153^{th}$ amino acid residue (valine) of the α subunit is substituted with an amino acid selected from isoleucine, leucine, methionine and threonine
(h) the $154^{th}$ amino acid residue (tryptophane) of the α subunit is substituted with leucine Meanwhile, also included in the improved nitrile hydratase of the invention is a nitrile hydratase that is homologous or identical to the amino acid sequence described in SEQ ID NO: 4 at approximately 70% or higher, preferably at approximately 80% or higher, more preferably at approximately 90% or higher, even more preferably at approximately 95% or higher, and particularly preferably at approximately 98% or higher, at a position other than the aforementioned substitution portions, and also has the same heat resistance and/or resistance to amide compounds.

Furthermore, regarding the amino acid sequence identified as SEQ ID NO: 4, a nitrile hydratase having, at a substation position other than those described above, an amino acid sequence in which 1 to 10, preferred to be approximately 1 to 5, and even more preferably 1 to 2 amino acid residues are deleted, substituted, or added and having the same heat resistance and/or resistance to amide compounds is also included in the improved nitrile hydratase of the invention.

The above amino acid substitutions of (e) to (h) are described as "Y α 8G, S α 88V, V α 153I, W α 154L". Standard amino acids are identified by a single-letter alphabetic code. The letter to the left of the numeral showing the substituted position (i.e., number of amino acid residues to the substituted site) represents the amino acid in a one-letter code before substitution, and the letter to the right represents the amino acid in a one-letter code after substitution.

In particular, regarding the amino acid sequence of the α subunit as shown in SEQ ID NO: 4, if there is a description of "Y α 8G", it means an embodiment of having amino acid substitution in the improved nitrile hydratase in which tyrosine (Y) at position 8 counted from the N-terminal amino acid residue (including the N-terminal amino acid residue itself) of the amino acid sequence of the α subunit (SEQ ID NO: 4) is substituted with glycine (G).

Modes of amino acid substitutions in more preferred embodiments of the improved nitrile hydratase according to the invention are shown as the following 1 to 8:

1. Y α 8G
2. Y α 8V

3. S α 88V
4. S α 88T
5. V α 153I
6. V α 153L
7. V α 153M
8. V α 153T
9. W α 154L

Preferred embodiments of base substitutions to cause the above amino acid substitutions are shown below.

TABLE 1

| | |
|---|---|
| Yα8G | Codon TAC (at positions 22~24 in SEQ ID NO: 3) is preferred to be substituted with GGT, GGC, GGA, GGG. Especially preferred to be substituted is T at position 22 with G, and A at position 23 with G (TAC→GGC). |
| Yα8V | Codon TAC (at positions 22~24 in SEQ ID NO: 3) is preferred to be substituted with GTT, GTC, GTA, GTG. Especially preferred to be substituted is T at position 22 with G, and A at position 23 with T (TAC→GTC). |
| Yα8T | Codon TAC (at positions 22~24 in SEQ ID NO: 3) is preferred to be substituted with ACA, ACC, AACG, ACT. Especially preferred to be substituted is T at position 22 with A, and A at position 23 with C (TAC→ACC). |
| Sα88V | Codon TCG (at positions 262~264 in SEQ ID NO: 3) is preferred to be substituted with GTT, GTC, GTA, GTG. Especially preferred to be substituted is T at position 262 with T, C at position 263 with T, G at position 263 with C (GTT→GTC). |
| Sα88T | Codon TCG (at positions 262~264 in SEQ ID NO: 3) is preferred to be substituted with ACA, ACC, ACG, ACT. Especially preferred to be substituted is T at position 262 with A (TCG→ACG). |
| Vα153I | Codon GTT (at positions 457~459 in SEQ ID NO: 3) is preferred to be substituted with ATT, ATC, ATA. Especially preferred to be substituted is G at position 457 with A, and T at position 459 with C (GTT→ATC). |
| Vα153L | Codon GTT (at positions 457~459 in SEQ ID NO: 3) is preferred to be substituted with TTA, TTG, CTT, CTC, CTA, CTG. Especially preferred to be substituted is G at position 457 with C (GTT→CTC). |
| Vα153T | Codon GTT (at positions 457~459 in SEQ ID NO: 3) is preferred to be substituted with ACT, ACC, ACA, ACG. Especially preferred to be substituted is G at position 457 with A, T at position 458 with C, T at position 459 with C (GTT→ACC). |
| Vα153M | Codon GTT (at positions 457~459 in SEQ ID NO: 3) is preferred to be substituted with ATG. |
| Wα154L | Codon TGG (at positions 460~462 in SEQ ID NO: 3) is preferred to be substituted with TTA, TTG, CTT, CTC, CTA, CTG. Especially preferred to be substituted is G at position 461 with T (TGG→TTG). |

With regard to the activity of the improved nitrile hydratase of the invention, resistance to amide compounds under high temperatures is improved relative to the activity of the wild type nitrile hydratase while naturally derived characteristics are maintained.

Here, "nitrile hydratase activity" means an enzyme activity to catalyze the hydration for converting a nitrile compound to a corresponding amide compound (RCN+ $H_2O \rightarrow RCONH_2$). Determining the activity is conducted by bringing a nitrile compound as a substrate into contact with a nitrile hydratase for conversion to a corresponding amide compound and by quantifying the resultant amide compound. Any nitrile compound may be used as a substrate as long as nitrile hydratase reacts with such a compound, but acrylonitrile is preferred.

Reaction conditions include a substrate concentration of 2.5%, reaction temperature of 10° C. to 30° C. and reaction time of 10 to 30 minutes. The enzymatic reactions are terminated by adding phosphoric acid. Then, using HPLC (high-performance liquid chromatography) or gas chromatography, the produced acrylamide is analyzed to measure the amount of the amide compound.

The expression "resistance to amide compounds under high temperatures" means that, even in the presence of amide compounds, the nitrile hydratase activity is maintained under high temperatures. The expression "high temperatures" indicate specifically 40° C. to 60° C., and more preferably 45° C. to 55° C.

The "resistance to amide compounds under high temperatures" can be evaluated by analyzing a culture of transformant containing an improved nitrile hydratase, or an improved nitrile hydratase isolated from the transformant in the presence of an amide compound such as acrylamide (at a high concentration of 30 to 50%, for example) under high temperatures based on the consumption amount or consumption rate of a nitrile compound such as acrylonitrile as substrate. For example, when the improved nitrile hydratase is brought into contact with an amide compound in the range of 40° C. to 60° C. and the nitrile hydratase shows the consumption amount or consumption rate of 1.1 times or more, preferably 1.15 times or more, and more preferably 1.2 times or more that of the comparative example (i.e., nitrile hydratase with no mutation), it can be evaluated that to be resistant to amide compounds under high temperatures.

As for the "amide compounds", an amide compound represented by the general formula (1) below, for example, can be mentioned.

$$R-CONH_2 \qquad (1)$$

(in the formula R is an optionally substituted linear or branched alkyl or alkenyl group having 1 to 10 carbon atoms, an optionally substituted cycloalkyl or aryl group having 3 to 18 carbon atoms, or an optionally substituted saturated or unsaturated heterocyclic group). Particularly preferred is an acrylamide in which "R" in the formula is "$CH_2=CH-$."

The above improved nitrile hydratase is obtained by performing amino acid substitution on a known nitrile hydratase. For example, such an improved nitrile hydratase is obtained by introducing the aforementioned mutation to the amino acid sequence (SEQ ID NO: 4) of a nitrile hydratase derived from *Rhodococcus rhodochrous* J1 strain, and by screening a nitrile hydratase with an improved resistance to amide compound at high temperatures.

Even for a nitrile hydratase derived from those other than J1 strain, resistance to amide compounds under high temperatures can be enhanced by introducing the same mutation to a corresponding site for modification. Examples of the bacteria for producing a nitrile hydratase include *Rhodococcus rhodochrous* M8 (SEQ ID NO: 5), *Rhodococcus ruber* TH (SEQ ID NO: 6), *Rhodococcus rhodochrous* M33 (VKM Ac-1515D), *Rhodococcus pyridinivorans* MW3 (SEQ ID NO: 7), *Rhodococcus pyridinivorans* S85-2 (SEQ ID NO: 8), *Nocardia* sp. JBRs (SEQ ID NO: 10), and *Nocardia* YS-2002 (SEQ ID NO: 11). Meanwhile, *Rhodococcus rhodochrous* M33 (VKM Ac-1515D) was selected because it is capable of constitutive expression of a nitrile hydratase based on natural mutation of the above M8 bacteria and the amino acid or gene sequence of the nitrile hydratase itself is not mutated (U.S. Pat. No. 5,827,699).

The improved nitrile hydratase of the invention can be obtained by introducing a mutation, either randomly or site-specifically, to a gene encoding a known nitrile hydratase according to a known method, and selecting the enzyme with desired function, i.e., resistance to amide compounds under high temperatures.

Examples of a method for introduction a mutation include a random mutation introduction method like error prone PCR and site-directed mutagenesis like Kunkel method or Gapped Duplex method.

[Error Prone PCR]

As a method for studying functions and characteristics of proteins using a mutant, random mutagenesis is known. Random mutagenesis is a method to introduce a random mutation to the gene encoding a specific protein so that a mutant is produced. In random mutagenesis by PCR, stringency conditions are set low for the DNA amplification period so that a mutant base can be introduced (error-prone PCR).

In such an error-prone PCR method, a mutation is introduced randomly into any position of the entire DNA site to be amplified. Then, by examining the function of the obtained mutant, in which the mutation is introduced at a random site, information of the amino acid or domain important for a specific function of a protein is obtained. As a nitrile hydratase used for the template of error-prone PCR, the nitrile hydratase gene derived from a wild-type strain or DNA obtained as an amplified product by error-prone PCR can be used.

As reaction conditions for error-prone PCR, for example, a composition ratio of any one, two or three among dNTP (dGTP, dCTP, dATP or dTTP) in the reaction mix is reduced relative to another dNTP. Accordingly, during the DNA synthesis, at a position that requires a dNTP whose ratio is reduced, another dNTP is more likely to be used by error and that may lead to mutation. In addition, other preferred reaction conditions are a composition in which the amount of $MgCl_2$ and/or $MnCl_2$ in the reaction mix is increased.

[Site-Directed Mutagenesis (Site-Specific Introduction of Mutation)]

As for the method for introducing a mutation to a specific site, a general method is as follows: the DNA chain containing a target gene is dissociated into a single strand, and annealed to an oligonucleotide chain containing a target gene, which is then prepared as a double strand by elongating the single stand using a DNA polymerase, the double strand is combined in *E. coli* for replication, and, after replication by fusion in *E. coli*, a clone including the desired mutation is selected (see, Molecular Cloning, A Laboratory Manual 2nd ed., Cold Spring Harbor Laboratory Press (1989), Current Protocols in Molecular Biology, John Wiley & Sons (1987-1997) or the like). Other than Kunkel method, various methods such as Gapped Duplex method are known, and the method can be conveniently carried out by using a commercially available mutagenesis kit such as Quick-Change™ XL Site-Directed Mutagenesis Kit (manufactured by Stratagene), GeneTailor™ Site-Directed Mutagenesis System (manufactured by Invitrogen Corporation), TaKaRa Site-Directed Mutagenesis System (Mutan-K, Mutan-Super Express Km and the like, manufactured by Takara Bio Inc.), or the like.

Other than the method including introduction of a mutation to a gene of known nitrile hydratase as described above, the improved nitrile hydratase of the invention can be also obtained by metagenome screening from environmental DNA.

1.3 DNA Encoding Improved Nitrile Hydratase

The invention also provides DNA encoding the improved nitrile hydratase of the invention.

The "DNA encoding the improved nitrile hydratase" of the invention also includes DNA which is hybridized under stringent conditions with a DNA having a base sequence complementary to the base sequence of the DNA encoding the improved nitrile hydratase of the invention, and also encodes a protein with nitrile hydratase activity which has resistance to amide compounds under high temperatures.

"Stringent conditions" are those for washing after hybridization; a salt concentration of 300 to 2000 mM and a temperature of 40 to 75° C., preferably a salt concentration of 600 to 900 mM and a temperature of 65° C. For example, conditions 2×SSC at 50° C. may be employed. In addition to such a salt concentration of the buffer, temperature and the like, a person skilled in the art may set conditions for obtaining DNA that encodes a nitrile hydratase of the invention by adding various conditions such as probe concentration, probe length, reaction time, and the like.

For detailed order of hybridization, Molecular Cloning, A Laboratory Manual, 2nd edition (Cold Spring Harbor Laboratory Press (1989)) or the like may be referred to. DNA to be hybridized includes DNA or its partial fragment, containing a base sequence which has 40% or greater, preferably 60% or greater, and more preferably 90% or greater sequence homology to the gene DNA of the invention.

1.4 Recombinant Vector, Transformant

It is necessary for the DNA encoding the improved nitrile hydratase gene to be implanted into a vector so that nitrile hydratase is expressed in the host organism to be transformed. Examples of such vectors to be used include plasmid DNA, bacteriophage DNA, retrotransposon DNA, artificial chromosome DNA and the like.

In addition to a nitrile hydratase gene, a vector may be coupled with a promoter, terminator, enhancer, splicing signal, poly A addition signal, selection marker, ribosome binding sequence (SD sequence) or the like. Examples of the selection markers include kanamycin resistance gene, dihydrofolate reductase gene, ampicillin resistance gene, neomycin resistance gene and the like.

A host to be used in the invention is not limited to any specific type as long as it can express the target nitrile hydratase after the recombinant vector is introduced into the host. Examples include bacteria such as *E. coli* and *Bacillus subtilis*, yeasts, animal cells, insect cells, plant cells and the like.

When *E. coli* is used as a host, an expression vector with high expression efficiency, such as expression vector pkk 233-2 with a trc promoter (manufactured by Amersham Biosciences Corp.), pTrc 99A (manufactured by Amersham Biosciences Corp.) or the like, is preferred.

When a bacterium is used as a host, *Escherichia coli* may be used, for example, and a *Rhodococcus* strain such as *Rhodococcus rhodochrous* ATCC 12674, *Rhodococcus rhodochrous* ATCC 17895 and *Rhodococcus rhodochrous* ATCC 19140 may also be used. Those ATCC strains can be obtained from the American type culture collection. Method for introducing a recombinant vector into a bacterium is not limited to any specific method as long as DNA is introduced into the bacterium. For example, a method using calcium ions, electroporation or the like may be employed.

When yeast is used as a host, examples are *Saccharomyces cerevisiae, Schizosaccharomyces pombe, Pichia pastoris* and the like. As a method for introducing a recombinant vector into yeast, it is not limited specifically as long as DNA can be introduced into the yeast. For example, an electroporation method, spheroplast method, lithium acetate method or the like may be employed.

When animal cells are used as a host, monkey cells COS-7, Vero, CHO cells, mouse L cells, rat GH3 cells, human FL cells or the like may be employed. As a method for introducing a recombinant vector into animal cells, for example, an electroporation method, calcium phosphate method, lipofection method or the like may be used.

When insect cells are used as a host, Sf9 cells, Sf21 cells or the like may be used. A method for introducing a recombinant vector into insect cells, for example, a calcium phosphate method, lipofection method, electroporation method or the like may be used.

When plant cells are used as a host, tobacco BY-2 cells or the like may be used, but not limited to them. A method for introducing a recombinant vector into plant cells, for example, an *Agrobacterium* method, particle gun method, PEG method, electroporation method or the like may be used.

When *E. coli* is used as a host, since most of the expressed nitrile hydratase is formed as an inclusion body and is insoluble, a transformant with low catalytic activity is obtained. On the other hand, if a *Rhodococcus* strain is used as a host, nitrile hydratase is present in the soluble fraction, and thus a transformant with high activity is obtained. The host may be selected based on purposes. However, when an improved enzyme is selected under stringent conditions, a transformant with high activity derived from a *Rhodococcus* strain is preferred.

1.5 Method for Producing Improved Nitrile Hydratase

The improved nitrile hydratase can be produced by culturing the above transformant and collecting a protein with nitrile hydratase activity from the obtained culture. The invention also provides such a method for producing an improved nitrile hydratase.

In the invention, "culture" means any of culture supernatant, cultured cell, cultured bacterial-cell, and cell homogenates or bacterial-cell homogenates.

Culture of a transformant is carried out according to a method which is generally used for culture of a host. As for a medium to culture a transformant of the invention, a natural or synthetic culture medium is used as long as it contains a carbon source, a nitrogen source, inorganic salts or the like for the host bacteria to assimilate, and culture of a transformant is performed efficiently. Examples of a carbon source include carbohydrates such as glucose, galactose, fructose, sucrose, raffinose and starch; organic acids such as acetic acid and propionic acid; alcohols such as ethanol and propanol; and the like. Examples of a nitrogen source include inorganic acids such as ammonia, ammonium chloride, ammonium sulfate, ammonium acetate and ammonium phosphate; ammonium salts of organic acids; and other nitrogen-containing compounds.

In addition, peptone, yeast extract, meat extract, corn steep liquor, various amino acids or the like may also be used. Examples of an inorganic substance include monopotassium phosphate, dipotassium phosphate, magnesium phosphate, magnesium sulfate, sodium chloride, ferrous sulfate, manganese sulfate, zinc sulfate, copper sulfate, calcium carbonate and the like. Also, if necessary, a defoaming agent may be used to prevent foaming during the culture process. Moreover, cobalt ions or iron ions as prosthetic molecules of a nitrile hydratase, or nitriles and amides as an inducer of the enzyme, may also be added to the culture.

Culture may be conducted by adding selective pressure to prevent the vector and the target gene from being eliminated. Namely, if a selection marker is a drug-resistant gene, a corresponding drug may be added; or if a selection marker is an auxotrophic complementary gene, corresponding nutrition factors may be removed.

Also, if a selection marker is an assimilation adding gene, an equivalent assimilation factor may be added as a sole factor, if necessary. For example, when *E. coli* transformed by a vector containing an ampicillin-resistant gene is cultured, ampicillin may be added as needed during the culture process.

When culturing a transformant transformed by a recombinant vector containing, as a promoter, an inducible promoter, such an inducer may be added to the medium, if necessary. For example, when culturing a transformant transformed by an expression vector with a promoter inducible with isopropyl-β-D-thiogalactopyranoside (IPTG), IPTG or the like may be added to the medium. Likewise, when culturing a transformant transformed by an expression vector with a trp promoter inducible with indoleacetic acid (IAA), IAA or the like may be added to the medium.

Culture conditions of a transformant are not limited specifically as long as the productivity of the target improved nitrile hydratase and growth of the host are not prohibited. Generally, conditions are preferred to be 10° C. to 40° C., more preferably 20° C. to 37° C., for 5 to 100 hours. The pH value is adjusted using inorganic or organic acid, alkaline solution or the like. If it is *Rhodococcus*, the pH is adjusted to be 6 to 9.

As for culture methods, solid-state culture, static culture, shaking culture, aeration-agitation culture and the like may be used. When a *Rhodococcus* transformant is cultured, in particular, it is preferred to use shaking culture or aeration-agitation culture (jar fermentation) under aerobic conditions.

When cultured in culture conditions above, the improved nitrile hydratase of the invention is accumulated at a high yield in the above culture product namely, at least in any of culture supernatant, cultured cell, cultured bacterial-cell, cell homogenates or bacterial-cell homogenates.

After culture, when an improved nitrile hydratase is produced in a cell or bacterial cell, the target nitrile hydratase can be collected by homogenizing the cells or bacterial cells. Cells or bacterial cells are homogenized by high-pressure treatment using a French press or homogenizer, supersonic treatment, grinding treatment using glass beads or the like, enzyme treatment using lysozyme, cellulase, pectinase and the like, freezing and thawing treatment, hypotonic solution treatment, bacteriolysis induction treatment by phage, and so on.

After homogenization, residues of cell homogenates or bacterial-cell homogenates (including insoluble fractions of the cell extract) are removed, if necessary. To remove residues, centrifugal or filtration methods are employed, if necessary. To increase the efficiency of removing residues, a coagulant or filter aid may be used. The supernatant obtained after the removal of residues is soluble fractions of the cell extract, which can be used as a crudely purified improved nitrile hydratase solution.

Also, when an improved nitrile hydratase is produced in a bacterial cells or in cells, it is also possible that the bacterial cells or the cells themselves are collected by a centrifuge or membrane filtration and to be used without homogenizing them.

When an improved nitrile hydratase is produced outside cells or bacterial cells, the culture may be used as is, or the cells or bacterial cells are removed using a centrifugal or filtration method. Then, the improved nitrile hydratase is collected from the culture by being extracted through ammonium sulfate precipitation, if necessary. Furthermore, dialysis or various chromatography techniques (gel filtration, ion exchange chromatography, affinity chromatography, etc.) may be used to isolate and purify the nitrile hydratase.

The efficiency for producing a nitrile hydratase, which is obtained by culturing a transformant, can be confirmed in a unit per culture solution, wet weight or dry weight of bacterial cells, protein of a crude enzyme solution or the like by SD S-PAGE (polyacrylamide gel electrophoresis), nitrile hydratase activity measurements or the like, but not particularly limited thereto. SDS-PAGE may be conducted by a method well known by a person skilled in the art. Also, as for the nitrile hydratase activity, the activity described above may be used.

Other than the methods described above, an improved nitrile hydratase may be produced using a cell-free protein synthesis system. In a cell-free protein synthesis system, a protein is synthesized in an artificial vessel such as a test tube using a cell extract. A cell-free protein synthesis system used in the present invention includes a cell-free transcription system that synthesizes RNA using DNA as a template.

In such a case, an organism corresponding to the above host corresponds to the organism from which the cell extract is derived. Here, for the cell extract, extracts of eukaryotic or prokaryotic origin, such as the extract from wheat germ, E. coli and the like, may be used. Such cell extracts may be concentrated or not.

The cell extract can be obtained by ultrafiltration, dialysis, polyethylene glycol (PEG) precipitation or the like, for example. In the invention, a commercially available kit may also be used for cell-free protein synthesis. Examples of such a kit include a reagent kit PROTEIOS™ (TOYOBO CO., LTD.), TNT™ system (Promega Corporation), a synthesizer PG-Mate™ (TOYOBO CO., LTD.), RTS (Roche Diagnostics K.K.) and the like.

An improved nitrile hydratase obtained by cell-free protein synthesis as described above can be also purified by properly selecting a chromatography type.

2. Method for Producing Amide Compound

The improved nitrile hydratase of the invention can be used as an enzyme catalyst for material production. For example, an amide compound is produced by bringing a nitrile compound into contact with the improved nitrile hydratase. Then, the amide compound produced upon contact is collected. Accordingly, an amide compound is produced.

As an enzyme catalyst, in addition to the isolated and purified nitrile hydratase as described above, a culture after culturing the transformant of the invention or a processed product of the culture may also be used. Examples of the processed product include the cells after culture (i.e., transformant) immobilized with acrylamide gel or the like, those processed by glutaraldehyde, those supported by inorganic carriers such as alumina, silica, zeolite, diatomaceous earth and the like.

Here, "contact" means that an improved nitrile hydratase and a nitrile compound are present in the same reaction system or culture system: for example, an isolated and purified improved nitrile hydratase and a nitrile compound are mixed; a nitrile compound is added into a culture vessel of a cell (transformant) to express an improved nitrile hydratase gene; the cells are cultured in the presence of a nitrile compound; an extract of the cells is mixed with a nitrile compound; and so on.

A nitrile compound to be used as a substrate is selected by considering the substrate specificity of the enzyme, stability of the enzyme for the substrate and the like. As for the nitrile compound, acrylonitrile is preferred. The reaction method and the method for collecting an amide compound after the completion of reactions are properly selected depending on the characteristics of the substrate and the enzyme catalyst.

The enzyme catalyst is preferred to be recycled as long as its activity is not lost. From the viewpoint of preventing the loss of activity and easy recycling, the enzyme catalyst is preferred to be used as a processed product.

EXAMPLES

Hereinbelow, the invention is more specifically explained in view of the examples. However, the invention is not limited to them. Meanwhile, "%" described herein indicates % by mass.

Example 1

Preparation of Plasmid for Expressing Improved Nitrile Hydratase

A plasmid to be a template for introducing the amino acid substitution of the invention was prepared as follows.

As a template having the nitrile hydratase gene of the J1 strain, pSJ034 was used (FIG. 1). pSJ034 is a plasmid which is capable of expressing nitrile hydratase in a Rhodococcus strain. Plasmid pJD034 was produced from pSJ023 by the method disclosed in JP 10-337185 A. Namely, according to partial cleave at the XbaI site and ligation with the Sse8387I linker, plasmid pSJ033 was prepared so that one XbaI site of plasmid pSJ023 was substituted with Sse8387I. Next, plasmid pSJ033 was partially cleaved at the Sse8387I site, and a Klenow fragment was used to blunt the ends so as to cause self ligation. Accordingly, plasmid pSJ034 was obtained.

Here, Rhodococcus rhodochrous J-1 strain has been registered under accession number "FERM BP-1478" at the International Patent Organism Depositary, National Institute of Advanced Industrial Science and Technology (Central 6, 1-1-1 Higashi, Tsukuba, Ibaraki, (presently, NITE Patent Microorganisms Depositary Center: 2-5-8 Kazusakamatari, Kisarazu-shi, Chiba, Room No. 120)), (original deposition date of Sep. 18, 1987).

In addition, pSJ023 is a transformant "R. rhodochrous ATCC 12674/pSJ023," and is internationally registered under accession number FERM BP-6232 at the International Patent Organism Depositary, National Institute of Advanced Industrial Science (Central 6, 1-1-1 Higashi, Tsukuba, Ibaraki, (presently, NITE Patent Microorganisms Depositary Center: 2-5-8 Kazusakamatari, Kisarazu-shi, Chiba, Room No. 120)), (original deposition date of Mar. 4, 1997).

Example 2

Production of Improved Nitrile Hydratase

By using the plasmid pSJ034 prepared in Example 1, the amino acid substitution was performed. PCR was performed by using the composition of a reaction solution, reaction condition, and primers described below.

<Composition of PCR Reaction Solution>

| | |
|---|---|
| Sterile water | 20 μl |
| pSJ034 (1 ng/ml) | 1 μl |
| Forward Primer (10 mM) | 2 μl |
| Reverse Primer (10 mM) | 2 μl |
| PrimeSTAR MAX (2x) | 25 μl |
| Total | 50 μl |

<Reaction Conditions for PCR>
(98° C. for 10 seconds, 55° C. for 5 seconds, and 72° C. for 90 seconds)×30 cycles

TABLE 2

| <Primer> | | |
|---|---|---|
| Name of Primer | Sequence (5'-3') | SEQ ID NO |
| α8G-F | AATAAGGGCACGGAGTACGAGGCACGT | 20 |
| α8G-R | CTCCGTGCCCTTATTGACGTGCTCGCT | 21 |
| α8V-F | AATAAGGTCACGGAGTACGAGGCACGT | 22 |
| α8V-R | CTCCGTGACCTTATTGACGTGCTCGCT | 23 |
| α88V-F | CCAAATTGTCGCGGTCTTCAACGACTC | 24 |
| α88V-R | GACCGCGACAATTTGGTGTGCCTGCTC | 25 |
| α88T-F | CCAAATTACCGCGGTCTTCAACGACTC | 53 |
| α88T-R | GACCGCGGTAATTTGGTGTGCCTGCTC | 54 |
| α153I-F | GTCAGGATCTGGGACAGCAGCTCCGAA | 26 |
| α153I-R | GTCCCAGATCCTGACCTCCACCTCATC | 27 |
| α153L-F | GTCAGGCTCTGGGACAGCAGCTCCGAA | 28 |
| α153L-R | GTCAGGGAGTGGGACAGCAGCTCCGAA | 29 |
| α153M-F | GTCAGGATGTGGGACAGCAGCTCCGAA | 30 |
| α153M-R | GTCAGGCATTGGGACAGCAGCTCCGAA | 31 |
| α153T-F | GTCAGGACCTGGGACAGCAGCTCCGAA | 32 |
| α153T-R | GTCAGGGGTTGGGACAGCAGCTCCGAA | 33 |
| α154L-F | AGGGTTCTCGACAGCAGCTCCGAAATC | 34 |
| α154L-R | GCTGTCGAGAACCCTGACCTCCACCTC | 35 |
| α153I• α154L-F | GTCAGGATCCTCGACAGCAGCTCCGAA | 36 |
| α153I• α154L-R | GCTGTCGAGGATCCTGACCTCCACCTC | 37 |
| α153L• α154L-F | GTCAGGCTCCTCGACAGCAGCTCCGAA | 38 |
| α153L• α154L-R | GCTGTCGAGGAGCCTGACCTCCACCTC | 39 |
| α153M• α154L-F | GTCAGGATGCTCGACAGCAGCTCCGAA | 40 |
| α153M• α154L-R | GCTGTCGAGCATCCTGACCTCCACCTC | 41 |
| α153T• α154L-F | GTCAGGACCCTCGACAGCAGCTCCGAA | 42 |
| α153T α154L-R | GCTGTCGAGGAGCCTGACCTCCACCTC | 43 |

After the completion of PCR, 5 μL of the reaction mixture was provided for 0.7% agarose gel electrophoresis, an amplified fragment of 11 kb was confirmed, and 1 μL DpnI (provided with the kit) was added to the PCR reaction mixture, which was then reacted at 37° C. for an hour. Accordingly, the template plasmid was removed. After that, the reaction mixture was purified using Wizard SV Gel and PCR Clean-Up System (Promega Corporation), and transformation was introduced into JM109 using the purified PCR reaction product. From the obtained culture product, plasmid DNA was extracted using QIAprep Spin Miniprep Kit (Qiagen), and the base sequence of the nitrile hydratase was confirmed using automated sequencer CEQ 8000 (manufactured by Beckman Coulter, Inc.). Obtained plasmids were named as shown in Table 3.

TABLE 3

| Name of Plasmid | Amino acid substitutions |
|---|---|
| pSJ034 (Comparative example) | |
| pSJH001 | Yα8G |
| pSJH002 | Sα88V |
| pSJH064 | Sα88T |
| pSJH004 | Vα153M |
| pSJH005 | Wα154L |
| pSJH022 | Sα88V, Vα153M |
| pSJH023 | Sα88V, Vα153M, Wα154L |
| pSJH024 | Yα8G, Sα88V |
| pSJH025 | Yα8G, Vα153M |
| pSJH026 | Yα8V, Wα154L |
| pSJH027 | Yα8V, Vα153I |
| pSJH028 | Yα8G, Sα88V, Vα153I |
| pSJH030 | Yα8V, Vα153T, Wα154L |
| pSJH032 | Yα8G, Sα88V, Vα153M, Wα154L |

Example 3

Preparation of *Rhodococcus* Transformant

Cells of *Rhodococcus rhodochrous* strain ATCC 12674 in a logarithmic growth phase were collected using a centrifuge, washed three times with ice-cold sterile water, and suspended in the sterile water. Then, 1 μL of plasmid prepared in Example 2 and 10 μL of the bacterial-cell suspension were mixed and ice-cooled. The DNA and the bacterial-cell suspension were supplied in a cuvette, and electric pulse treatment was conducted using an electroporation device, Gene Pulser (Bio-Rad Laboratories), under conditions of 2.0 kV and 200Ω. The electric-pulse processed mixture was let stand in an ice-cold condition for 10 minutes, and subjected to heat shock at 37° C. for 10 minutes. After 500 μL of an MYK culture medium (0.5% polypeptone, 0.3% Bacto yeast extract, 0.3% Bacto malt extract, 0.2% K$_2$HPO$_4$, 0.2% KH$_2$PO$_4$) was added and let stand at 30° C. for 5 hours, the strain was applied onto an MYK agar culture medium containing 50 μg/mL kanamycin and cultured at 30° C. for 3 days. The obtained colony after culturing at 30° C. for 3 days was used as a transformant.

Each transformant obtained above process was inoculated into an MYK culture medium (50 μg/mL kanamycin), and subjected to shaking culture at 30° C. for 2 days. Then, 1% culture was inoculated into a GGPK culture medium (1.5% glucose, 1% sodium glutamate, 0.1% yeast extract, 0.05% K$_2$HPO$_4$, 0.05% KH$_2$PO$_4$, 0.05% Mg$_2$O$_4$.7H$_2$O, 1% CoCl$_2$, 0.1% urea, 50 μg/mL kanamycin, pH 7.2), and subjected to shaking culture at 30° C. for 3 days. Bacterial cells were collected by using a centrifuge, and were washed with a 100 mM phosphate buffer (pH 7.0) to prepare a bacterial-cell suspension.

Example 4

Evaluation of Resistance to Amide Compounds Under High Temperatures

Resistance to amide compounds of the improved nitrile hydratase obtained in Example 3 was measured according to the following method.

0.2 mL of the bacterial-cell mixture and 4.8 mL of a 50 mM phosphate buffer (pH 7.0) were mixed, to which 5 mL of a 50 mM phosphate buffer (pH 7.0) containing 5.0% (w/v) acrylonitrile was further added. Next, the mixture was reacted while being shaken at 10° C. for 10 minutes. Then, bacterial cells were filtered and the amount of produced acrylamide was quantified by using gas chromatography.

<Analysis Conditions>
Analysis instrument: gas chromatograph GC2014 (manufactured by Shimadzu Corporation)
Detector: FID (detection at 200° C.)
Column: 1 m glass column filled with PoraPak PS (column filler manufactured by Waters Corporation)
Column temperature: 190° C.

Nitrile hydratase activity was determined by conversion from the amount of acrylamide. Here, regarding nitrile hydratase activity, the amount of enzyme to produce 1 μmol of acrylamide per 1 minute is set as 1 U.

Next, the test was carried out with the following composition for reaction solution and reactions conditions. Meanwhile, the each cell suspension used for the reaction was suitably diluted in with 100 mM phosphate buffer solution (pH 7.0) such that it has the same enzyme activity amount from the previously measured enzyme activity. As a comparative control, the comparative strain ATCC12674/pSJ034 was used.

<Composition of Reaction Solution>
50% Acrylamide solution 94 g
Acrylonitrile 3 g
1 M Phosphate buffer solution 1 g
Cell solution (with same enzyme activity unit (U) amount) 2 g <Reaction Conditions>
Reaction temperature 45° C.
Reaction time 3 hours 1 ml of each reaction solution was sampled either before the start of the reaction (0 hour) or 3 hours after the reaction. After filtering it using 0.45 μm filter, the obtained filter solution was subjected to gas chromatography. Result of analyzing the ratio of the remaining acrylonitrile (%) was shown in Table 4.

TABLE 4

| Name of Plasmid | Acrylonitrile consumption amount (%) | relative ratio (%) |
|---|---|---|
| pSJ034 (Comparative example) | 0.8 | 100% |
| pSJH001 | 1.0 | 125% |
| pSJH002 | 1.4 | 163% |
| pSJH064 | 0.88 | 110% |
| pSJH004 | 1.8 | 225% |
| pSJH005 | 1.1 | 138% |
| pSJH022 | 2.3 | 288% |
| pSJH023 | 2.6 | 325% |
| pSJH024 | 1.3 | 163% |
| pSJH025 | 2.3 | 288% |
| pSJH026 | 1.7 | 213% |
| pSJH027 | 1.5 | 188% |
| pSJH028 | 1.6 | 200% |
| pSJH030 | 2.4 | 300% |
| pSJH032 | 2.6 | 325% |

From the above results, it was found that the acrylonitrile consumption rate of every improved nitrile hydratase is 110% or more than pSJ034 as a comparative example. In a reaction for synthesizing amide compounds using a nitrile hydratase, a loss of the activity due to exposure to high temperature and high concentration of product, and an reaction inhibition caused by the amide compounds as a reaction product are the problems. In this regard, as the improved nitrile hydratase of the invention maintains the nitrile hydratase activity even at high temperature and even in the presence of acrylamide at high concentration, it is believed to have improved acrylamide resistance under high temperatures.

Example 5

Production of Improved Nitrile Hydratase

The amino acid substitution was performed in the same manner as Example 2 by using the nitrile hydratase described in WO 2012/164933 A (pSJ306A). The prepared plasmids are shown in Table 5.

TABLE 5

| Name of Plasmid | Amino acid substitutions |
|---|---|
| pSJ306A (Comparative example) | Pβ17G, Sβ57M, Tβ107K, Kβ114Y, Nβ167S, Cβ218H, Vβ219A, Gα174L |
| pSJA006 | Yα8G, Pβ17G, Sβ57M, Tβ107K, Kβ114Y, Nβ167S, Cβ218H, Vβ219A, Gα174L |
| pSJA018 | Yα8V, Pβ17G, Sβ57M, Tβ107K, Kβ114Y, Nβ167S, Cβ218H, Vβ219A, Gα174L |
| pSJB018 | Sα88V, Pβ17G, Sβ57M, Tβ107K, Kβ114Y, Nβ167S, Cβ218H, Vβ219A, Gα174L |
| pSJC008 | Vα153I, Pβ17G, Sβ57M, Tβ107K, Kβ114Y, Nβ167S, Cβ218H, Vβ219A, Gα174L |
| pSJC010 | Vα153L, Pβ17G, Sβ57M, Tβ107K, Kβ114Y, Nβ167S, Cβ218H, Vβ219A, Gα174L |
| pSJC017 | Vα153T, Pβ17G, Sβ57M, Tβ107K, Kβ114Y, Nβ167S, Cβ218H, Vβ219A, Gα174L |
| pSJC011 | Vα153M, Pβ17G, Sβ57M, Tβ107K, Kβ114Y, Nβ167S, Cβ218H, Vβ219A, Gα174L |
| pSJD010 | Wα154L, Pβ17G, Sβ57M, Tβ107K, Kβ114Y, Nβ167S, Cβ218H, Vβ219A, Gα174L |

TABLE 5-continued

| Name of Plasmid | Amino acid substitutions |
|---|---|
| pSJG001 | Sα88V, Vα153M, Pβ17G, Sβ57M, Tβ107K, Kβ114Y, Nβ167S, Cβ218H, Vβ219A, Gα174L |
| pSJG002 | Sα88V, Vα153M, Wα154L, Pβ17G, Sβ57M, Tβ107K, Kβ114Y, Nβ167S, Cβ218H, Vβ219A, Gα174L |
| pSJG003 | Sα88V, Vα153L, Wα154L, Pβ17G, Sβ57M, Tβ107K, Kβ114Y, Nβ167S, Cβ218H, Vβ219A, Gα174L |
| pSJG004 | Vα153M, Wα154L, Pβ17G, Sβ57M, Tβ107K, Kβ114Y, Nβ167S, Cβ218H, Vβ219A, Gα174L |
| pSJG005 | Vα153L, Wα154L, Pβ17G, Sβ57M, Tβ107K, Kβ114Y, Nβ167S, Cβ218H, Vβ219A, Gα174L |

By using the plasmids described in Table 5, *Rhodococcus rhodochrous* ATCC12674 transformant was obtained in the same manner as Example 3, and cultured in a MYK medium. By using the obtained culture cells, evaluation of the resistance to amide compounds under high temperatures was carried out according to the following conditions.
<Composition of Reaction Solution>
50% Acrylamide solution 94 g
Acrylonitrile 3 g
1 M Phosphate buffer solution 1 g
Cell solution (with same enzyme activity unit (U) amount) 1 g
<Reaction Conditions>
Reaction temperature 45° C.
Reaction time 5 hours

TABLE 6

| Name of Plasmid | Acrylonitrile consumption amount (%) | Acrylonitrile consumption rate (%) |
|---|---|---|
| pSJ306A (Comparative example) | 1.63 | 100% |
| pSJA006 | 2.16 | 133% |
| pSJA018 | 1.99 | 122% |
| pSJB018 | 1.79 | 110% |
| pSJC008 | 2.20 | 135% |
| pSJC010 | 2.41 | 148% |
| pSJC011 | 2.26 | 139% |
| pSJC017 | 2.42 | 148% |
| pSJD010 | 2.31 | 142% |
| pSJG001 | 2.26 | 139% |
| pSJG002 | 2.63 | 161% |
| pSJG003 | 2.68 | 164% |
| pSJG004 | 2.57 | 158% |
| pSJG005 | 2.38 | 146% |

From the above results, it was found that the acrylonitrile consumption rate of every improved nitrile hydratase is 110% or more than pSJ306A as a comparative example. Accordingly, as the improved nitrile hydratase of the invention maintains the nitrile hydratase activity even at high temperature, and even in the presence of high concentration of acrylamide, it is believed to have improved acrylamide resistance under high temperatures.

Example 6

Production of Improved Nitrile Hydratase (JBRs)

A plasmid for expressing the nitrile hydratase gene derived from *Nocardia* sp. JBRs (GenBank accession number: AY141130) was produced according to the following method.

By carrying out PCR in which pSJ034 is used as a template, the vector fragment was prepared using Wizard SV Gel and PCR Clean-Up System (Promega Corporation).
<Composition of PCR Reaction Solution>

| Sterile water | 20 µl |
|---|---|
| pSJ034 (1 ng/ml) | 1 µl |
| Forward Primer (10 mM) | 2 µl |
| Reverse Primer (10 mM) | 2 µl |
| PrimeSTAR MAX (2x) | 25 µl |
| Total | 50 µl |

<PCR Reaction Conditions>
(98° C. for 10 seconds, 55° C. for 5 seconds, and 72° C. for 90 seconds)×30 cycles (SEQ ID NO: 51)
NH-F: GAAGTGATCG TATGAGTGAA GACACACTCA CTG (SEQ ID NO: 52)
NH-R: GTGGATACCA TCCATTTCCT CATTCCTTTC ATC The vector fragment produced in the above and the artificially synthesized nitrile hydratase gene derived from *Nocardia* sp. JBRs (SEQ ID NO: 44) were cloned by using In-Fusion Cloning Kit (Takara Bio Inc.) and transformed into *E. coli* HST08 (Takara Bio Inc.). From the obtained colonies, the plasmid was collected and the DNA sequence was confirmed. Accordingly, the plasmid for expressing the nitrile hydratase derived from *Nocardia* sp. JBRs was obtained (pSJ-JBRs).

Furthermore, by using the pSJ-JBRs as a template, the amino acid substitution was performed in the same manner as Example 2. The produced plasmids are shown in Table 7.

TABLE 7

| Name of Plasmid | Amino acid substitutions from wild strain |
|---|---|
| pSJ-JBRs (Comparative example) | |
| pSJH006 | Yα8G |
| pSJH007 | Yα8V |
| pSJH061 | Sα88T |
| pSJH008 | Vα153L |
| pSJH009 | Vα153T |
| pSJH033 | Vα153L, Wα154L |
| pSJH034 | Sα88V, Vα153M, Wα154L |
| pSJH035 | Sα88V, Vα153T, Wα154L |
| pSJH036 | Yα8G, Sα88V |
| pSJH037 | Yα8V, Wα154L |
| pSJH038 | Yα8G, Sα88V, Vα153I |
| pSJH039 | Yα8G, Sα88V, Vα153L, Wα154L |
| pSJH040 | Yα8G, Sα88V, Vα153M, Wα154L |

By using the plasmids described in Table 7, *Rhodococcus rhodochrous* ATCC12674 transformant was obtained in the same manner as Example 3, and cultured in a MYK medium. By using the obtained culture cells, evaluation of the resistance to amide compounds under high temperatures was carried out according to the conditions of Example 4. The results are shown in Table 8.

TABLE 8

| Name of Plasmid | Acrylonitrile consumption amount (%) | Acrylonitrile consumption rate (%) |
|---|---|---|
| pSJ-JBRs (Comparative example) | 1.3 | 100% |
| pSJH006 | 1.45 | 112% |
| pSJH007 | 1.45 | 112% |
| pSJH061 | 1.6 | 125% |
| pSJH008 | 2.6 | 200% |
| pSJH009 | 1.9 | 146% |
| pSJH033 | 2.7 | 208% |
| pSJH034 | 2.7 | 208% |
| pSJH035 | 2.4 | 185% |
| pSJH036 | 1.4 | 108% |
| pSJH037 | 2.4 | 208% |
| pSJH038 | 1.5 | 123% |
| pSJH039 | 2.7 | 208% |
| pSJH040 | 2.7 | 208% |

From the above results, it was found that the acrylonitrile consumption rate of every improved nitrile hydratase is 108% or more than pSJ-JBRs as a comparative example. In this regard, as the improved nitrile hydratase of the invention maintains the nitrile hydratase activity even at high temperature, and even in the presence of high concentration of acrylamide, it is believed to have improved acrylamide resistance under high temperatures.

Example 7

Production of Improved Nitrile Hydratase (S85-2)

The plasmid for expressing the nitrile hydratase gene derived from *Rhodococcus pyridinivorans* S85-2 (GenBank accession number: AJ582605) was produced in the same manner as Example 6 by using an artificially synthesized nitrile hydratase gene (SEQ ID NO: 45). The obtained plasmid was named pSJ-S85-2.

Furthermore, by using the pSJ-S85-2 as a template, the amino acid substitution was performed in the same manner as Example 2. The produced plasmids are shown in Table 9.

TABLE 9

| Name of Plasmid | Amino acid substitutions from wild strain |
|---|---|
| pSJ-S85-2 (Comparative example) | |
| pSJH013 | Yα8V |
| pSJH014 | Vα153L |
| pSJH048 | Vα153L, Wα154L |
| pSJH049 | Sα88V, Vα153L, Wα154L |
| pSJH051 | Yα8G, Vα153M |
| pSJH052 | Yα8V, Wα154L |
| pSJH053 | Yα8V, Vα153L |

By using the plasmids described in Table 9, *Rhodococcus rhodochrous* ATCC12674 transformant was obtained in the same manner as Example 3, and cultured in a MYK medium. By using the obtained culture cells, evaluation of the resistance to amide compounds under high temperatures was carried out according to the conditions of Example 4. The results are shown in Table 10.

TABLE 10

| Name of Plasmid | Acrylonitrile consumption amount (%) | Acrylonitrile consumption rate (%) |
|---|---|---|
| pSJ-S85-2 (Comparative example) | 1.19 | 100% |
| pSJH013 | 1.70 | 143% |
| pSJH014 | 1.77 | 148% |
| pSJH048 | 2.59 | 218% |
| pSJH049 | 2.58 | 217% |
| pSJH051 | 2.59 | 218% |
| pSJH052 | 1.65 | 139% |
| pSJH053 | 1.87 | 158% |

From the above results, it was found that the acrylonitrile consumption rate of every improved nitrile hydratase is 130% or more than pSJ-S85-2 as a comparative example. In this regard, as the improved nitrile hydratase of the invention maintains the nitrile hydratase activity even at high temperature, and even in the presence of high concentration of acrylamide, it is believed to have improved acrylamide resistance under high temperatures.

Example 8

Production of Improved Nitrile Hydratase (M8)

As for the plasmid for expressing the nitrile hydratase gene derived from *Rhodococcus rhodochrous* M8 (GenBank accession number: AAT79340, AAT79339), plasmid pSJ-NO1A described in JP 2011-200132 A was used and the amino acid substitution was carried out in the same manner as Example 2. The prepared plasmids are shown in Table 11.

TABLE 11

| Name of Plasmid | Amino acid substitutions from wild strain |
|---|---|
| pSJ-NO1A (Comparative example) | None |
| pSJH010 | Sα88V |
| pSJH062 | Sα88T |
| pSJH011 | Vα153M |
| pSJH012 | Wα154L |
| pSJH041 | Sα88V, Vα153M |
| pSJH042 | Vα153M, Wα154L |
| pSJH044 | Yα8V, Vα153M |
| pSJH045 | Yα8V, Vα153I |
| pSJH046 | Yα8V, Vα153T, Wα154L |
| pSJH047 | Yα8V, Sα88V, Vα153T, Wα154L |

By using the plasmids described in Table 11, *Rhodococcus rhodochrous* ATCC12674 transformant was obtained in the same manner as Example 3, and cultured in a MYK medium. By using the obtained culture cells, evaluation of the resistance to amide compounds under high temperatures was carried out according to the conditions of Example 4. The results are shown in Table 12.

TABLE 12

| Name of Plasmid | Acrylonitrile consumption amount (%) | Acrylonitrile consumption rate (%) |
|---|---|---|
| pSJ-NO1A (Comparative example) | 1.39 | 100% |

TABLE 12-continued

| Name of Plasmid | Acrylonitrile consumption amount (%) | Acrylonitrile consumption rate (%) |
|---|---|---|
| pSJH010 | 1.60 | 115% |
| pSJH062 | 2.08 | 150% |
| pSJH011 | 2.57 | 185% |
| pSJH012 | 2.29 | 165% |
| pSJH041 | 1.91 | 137% |
| pSJH042 | 2.64 | 190% |
| pSIH044 | 2.57 | 185% |
| pSJH045 | 2.00 | 144% |
| pSJH046 | 2.40 | 173% |
| pSJH047 | 2.63 | 189% |

From the above results, it was found that the acrylonitrile consumption rate of every improved nitrile hydratase is 110% or more than pSJ-NO1A as a comparative example. In this regard, as the improved nitrile hydratase of the invention maintains the nitrile hydratase activity even at high temperatures, and even in the presence of high concentration of acrylamide, it is believed to have improved acrylamide resistance under.

Example 9

Rhodococcus Rhodochrous (Mitsui Bacterium)

As for the plasmid for expressing the nitrile hydratase gene derived from *Pseudonocardia thermophila* JCM 3095 (GenBank accession number: DD028560, DD028561), plasmid pSJ-NO2A described in JP 2011-200132 A was used and the amino acid substitution was carried out in the same manner as Example 2. The prepared plasmids are shown in Table 10.

TABLE 13

| Name of Plasmid | Amino acid substitutions from wild strain |
|---|---|
| pSJ-NO2A (Comparative example) | |
| pSJH021 | Wα160L (Corresponding to $X_{22}$ in SEQ ID NO: 49) |

By using the plasmids described in Table 13, *Rhodococcus rhodochrous* ATCC12674 transformant was obtained in the same manner as Example 3, and cultured in a MYK medium. By using the obtained culture cells, evaluation of the resistance to amide compounds under high temperatures was carried out according to the conditions of Example 4. The results are shown in Table 14.

TABLE 14

| Name of Plasmid | Acrylonitrile consumption amount (%) | Acrylonitrile consumption rate (%) |
|---|---|---|
| pSJ-NO2A (Comparative example) | 0.50 | 100% |
| pSJH021 | 1.20 | 240% |

From the above results, it was found that the acrylonitrile consumption rate of every improved nitrile hydratase is 240% than pSJ-NO2A as a comparative example. In this regard, as the improved nitrile hydratase of the invention maintains the nitrile hydratase activity even at high temperature, and even in the presence of high concentration acrylamide, it is believed to have improved acrylamide resistance under high temperatures.

INDUSTRIAL APPLICABILITY

Because the improved nitrile hydratase of the invention has enhanced resistance to acrylamide under high temperatures, a corresponding amide compound can be effectively produced from a nitrile compound, and thus the nitrile hydratase is useful for industrial production of amide compounds.

All the publications, patents, and patent applications cited in the invention are incorporated in this application by reference.

DEPOSITION NUMBER

*Rhodococcus rhodochrous* J1 STRAIN: FERM BP-1478
*R. rhodochrous* ATCC12674/pSJ023: FERM BP-6232

SEQUENCE LISTING FREE TEXT

SEQ ID NO: 20: α8G-F primer
SEQ ID NO: 21: α8G-R primer
SEQ ID NO: 22: α8V-F primer
SEQ ID NO: 23: α8V-R primer
SEQ ID NO: 24: α88V-F primer
SEQ ID NO: 25: α88V-R primer
SEQ ID NO: 26: α153I-F primer
SEQ ID NO: 27: α153I-R primer
SEQ ID NO: 28: α153L-F primer
SEQ ID NO: 29: α153L-R primer
SEQ ID NO: 30: α153M-F primer
SEQ ID NO: 31: α153M-R primer
SEQ ID NO: 32: α153T-F primer
SEQ ID NO: 33: α153T-R primer
SEQ ID NO: 34: α154L-F primer
SEQ ID NO: 35: α154L-R primer
SEQ ID NO: 36: α153I•α154L-F primer
SEQ ID NO: 37: α153I•α154L-R primer
SEQ ID NO: 38: α153L•α154L-F primer
SEQ ID NO: 39: α153L•α154L-R primer
SEQ ID NO: 40: α153M•α154L-F primer
SEQ ID NO: 41: α153M•α154L-R primer
SEQ ID NO: 42: α153T•α154L-F primer
SEQ ID NO: 43: α153T•α154L-R primer
SEQ ID NO: 46: Specific amino acid according to the invention
SEQ ID NO: 47: Specific amino acid according to the invention
SEQ ID NO: 48: Specific amino acid according to the invention
SEQ ID NO: 49: Specific amino acid according to the invention
SEQ ID NO: 50: Amino acid of the α subunit according to the invention
SEQ ID NO: 51: NH-F primer
SEQ ID NO: 52: NH-R primer
SEQ ID NO: 53: α88T-F primer
SEQ ID NO: 54: α88T-R primer

SEQUENCE LISTING

<160> NUMBER OF SEQ ID NOS: 57

<210> SEQ ID NO 1
<211> LENGTH: 690
<212> TYPE: DNA
<213> ORGANISM: Rhodococcus rhodochrous J-1

<400> SEQUENCE: 1

```
atggatggta tccacgacac aggcggcatg accggatacg gaccggtccc ctatcagaag      60
gacgagccct tcttccacta cgagtgggag ggtcggaccc tgtcaattct gacttggatg     120
catctcaagg gcatatcgtg gtgggacaag tcgcggttct ccgggagtc gatggggaac      180
gaaaactacg tcaacgagat cgcaactcg tactacaccc actggctgag tgcggcagaa      240
cgtatcctcg tcgccgacaa gatcatcacc gaagaagagc gaaagcaccg tgtgcaagag      300
atccttgagg tcggtacac ggacaggaag ccgtcgcgga agttcgatcc ggcccagatc       360
gagaaggcga tcgaacggct tcacgagccc cactccctag cgcttccagg agcggagccg      420
agtttctctc tcggtgacaa gatcaaagtg aagagtatga acccgctggg acacacacgg      480
tgcccgaaat atgtgcggaa caagatcggg gaaatcgtcg cctaccacgg ctgccagatc      540
tatcccgaga gcagctccgc cggcctcggc gacgatcctc gcccgctcta cggtcgcg       600
ttttccgccc aggaactgtg gggcgacgac ggaaacggga agacgtagt gtgcgtcgat       660
ctctgggaac cgtacctgat ctctgcgtga                                       690
```

<210> SEQ ID NO 2
<211> LENGTH: 229
<212> TYPE: PRT
<213> ORGANISM: Rhodococcus rhodochrous

<400> SEQUENCE: 2

```
Met Asp Gly Ile His Asp Thr Gly Gly Met Thr Gly Tyr Gly Pro Val
1               5                   10                  15

Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
        35                  40                  45

Asp Lys Ser Arg Phe Phe Arg Glu Ser Met Gly Asn Glu Asn Tyr Val
    50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ser Ala Gly Leu Gly Asp Asp
            180                 185                 190

Pro Arg Pro Leu Tyr Thr Val Ala Phe Ser Ala Gln Glu Leu Trp Gly
```

```
                195                 200                 205
Asp Asp Gly Asn Gly Lys Asp Val Val Cys Val Asp Leu Trp Glu Pro
            210                 215                 220

Tyr Leu Ile Ser Ala
225
```

<210> SEQ ID NO 3
<211> LENGTH: 612
<212> TYPE: DNA
<213> ORGANISM: Rhodococcus rhodochrous J-1

<400> SEQUENCE: 3

```
gtgagcgagc acgtcaataa gtacacggag tacgaggcac gtaccaaggc gatcgaaacc    60
ttgctgtacg agcgagggct catcacgccc gccgcggtcg accgagtcgt ttcgtactac   120
gagaacgaga tcggcccgat gggcggtgcc aaggtcgtgg ccaagtcctg ggtggaccct   180
gagtaccgca gtggctcga agaggacgcg acggccgcga tggcgtcatt gggctatgcc   240
ggtgagcagg cacaccaaat ttcggcggtc ttcaacgact cccaaacgca tcacgtggtg   300
gtgtgcactc tgtgttcgtg ctatccgtgg ccggtgcttg gtctcccgcc cgcctggtac   360
aagagcatgg agtaccggtc cgagtggta gcggaccctc gtggagtgct caagcgcgat   420
ttcggtttcg acatccccga tgaggtggag gtcagggttt gggacagcag ctccgaaatc   480
cgctacatcg tcatcccgga acggccgcc ggcaccgacg gttggtccga ggaggagctg   540
acgaagctgg tgagccggga ctcgatgatc ggtgtcagta atgcgctcac accgcaggaa   600
gtgatcgtat ga                                                      612
```

<210> SEQ ID NO 4
<211> LENGTH: 203
<212> TYPE: PRT
<213> ORGANISM: Rhodococcus rhodochrous

<400> SEQUENCE: 4

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175
```

Glu Glu Glu Leu Thr Lys Leu Val Ser Arg Asp Ser Met Ile Gly Val
            180                 185                 190

Ser Asn Ala Leu Thr Pro Gln Glu Val Ile Val
            195                 200

<210> SEQ ID NO 5
<211> LENGTH: 203
<212> TYPE: PRT
<213> ORGANISM: Rhodococcus rhodochrous M8

<400> SEQUENCE: 5

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
            195                 200

<210> SEQ ID NO 6
<211> LENGTH: 203
<212> TYPE: PRT
<213> ORGANISM: Rhodococcus ruber TH

<400> SEQUENCE: 6

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
        180                 185                 190

Ser Asn Ala Leu Thr Pro Gln Glu Val Ile Val
        195                 200

<210> SEQ ID NO 7
<211> LENGTH: 203
<212> TYPE: PRT
<213> ORGANISM: Rhodococcus pyridinivorans_MW3

<400> SEQUENCE: 7

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
        180                 185                 190

Ser Asn Ala Leu Thr Pro Gln Glu Val Ile Val
        195                 200

<210> SEQ ID NO 8
<211> LENGTH: 203
<212> TYPE: PRT
<213> ORGANISM: Rhodococcus pyridinivorans S85-2

<400> SEQUENCE: 8

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 9
<211> LENGTH: 203
<212> TYPE: PRT
<213> ORGANISM: Rhodococcus pyridinivorans MS-38

<400> SEQUENCE: 9

Val Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 10
<211> LENGTH: 203
<212> TYPE: PRT
<213> ORGANISM: Nocardia

<400> SEQUENCE: 10

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 11
<211> LENGTH: 203
<212> TYPE: PRT
<213> ORGANISM: Nocardia YS-2002

<400> SEQUENCE: 11

Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
            115                 120                 125

Val Val Ala Asp Pro Arg Gly Val Leu Lys Arg Asp Phe Gly Phe Asp
        130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
            180                 185                 190

Ser Asn Ala Leu Thr Pro Gln Glu Val Ile Val
            195                 200

<210> SEQ ID NO 12
<211> LENGTH: 180
<212> TYPE: PRT
<213> ORGANISM: Unknown
<220> FEATURE:
<223> OTHER INFORMATION: amino acid sequence of the alpha subunit of
      uncultured bacterium SP1

<400> SEQUENCE: 12

Met Ser Glu His Val Asn Lys Tyr Thr Glu Tyr Glu Ala Arg Thr Lys
1               5                   10                  15

Ala Val Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His His Val Val Val Cys Thr Leu Cys Ser Cys Tyr
                85                  90                  95

Pro Trp Pro Val Leu Gly Leu Pro Pro Ala Trp Tyr Lys Ser Met Glu
            100                 105                 110

Tyr Arg Ser Arg Val Val Ala Asp Pro Arg Gly Val Leu Lys Arg Asp
        115                 120                 125

Phe Gly Phe Asp Ile Pro Asp Glu Val Glu Val Arg Val Trp Asp Ser
    130                 135                 140

Ser Ser Glu Ile Arg Tyr Ile Val Ile Pro Glu Arg Pro Ala Gly Thr
145                 150                 155                 160

Asp Gly Trp Ser Glu Glu Glu Leu Thr Lys Leu Val Ser Arg Asp Ser
                165                 170                 175

Ile Ile Gly Val
            180

<210> SEQ ID NO 13
<211> LENGTH: 203
<212> TYPE: PRT
<213> ORGANISM: Unknown
<220> FEATURE:
<223> OTHER INFORMATION: amino acid sequence of the alpha subunit of
      uncultured bacterium BD2

<400> SEQUENCE: 13

Met Ser Glu His Val Asn Lys Tyr Thr Glu Tyr Glu Ala Arg Thr Lys
1               5                   10                  15

```
Ala Ile Glu Thr Leu Leu Tyr Glu Arg Gly Leu Ile Thr Pro Ala Ala
             20                  25                  30

Val Asp Arg Val Val Ser Tyr Tyr Glu Asn Glu Ile Gly Pro Met Gly
         35                  40                  45

Gly Ala Lys Val Val Ala Lys Ser Trp Val Asp Pro Glu Tyr Arg Lys
     50                  55                  60

Trp Leu Glu Glu Asp Ala Thr Ala Ala Met Ala Ser Leu Gly Tyr Ala
 65                  70                  75                  80

Gly Glu Gln Ala His Gln Ile Ser Ala Val Phe Asn Asp Ser Gln Thr
                 85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 14
<211> LENGTH: 203
<212> TYPE: PRT
<213> ORGANISM: Rhodococcus rhodocrous ATCC39484

<400> SEQUENCE: 14

Val Ser Glu His Val Asn Lys Tyr Thr Glu Tyr Glu Ala Arg Thr Lys
 1               5                  10                  15

Ala Ile Glu Thr Leu Leu Tyr Glu Arg Gly Leu Ile Thr Pro Ala Ala
             20                  25                  30

Val Asp Arg Val Val Ser Tyr Tyr Glu Asn Glu Ile Gly Pro Met Gly
         35                  40                  45

Gly Ala Lys Val Val Ala Lys Ser Trp Val Asp Pro Glu Tyr Arg Lys
     50                  55                  60

Trp Leu Glu Glu Asp Ala Thr Ala Ala Met Ala Ser Leu Gly Tyr Ala
 65                  70                  75                  80

Gly Glu Gln Ala His Gln Ile Ser Ala Val Phe Asn Asp Ser Gln Thr
                 85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Glu Ile
145                 150                 155                 160

Arg Tyr Ile Val Ile Pro Glu Arg Pro Ala Gly Thr Asp Gly Trp Ser
                165                 170                 175

Glu Asp Glu Leu Ala Lys Leu Val Ser Arg Asp Ser Met Ile Gly Val
```

```
                180                 185                 190
Ser Asn Ala Leu Thr Pro Gln Glu Val Ile Val
            195                 200
```

<210> SEQ ID NO 15
<211> LENGTH: 213
<212> TYPE: PRT
<213> ORGANISM: Sinorhizobium medicae WSM419

<400> SEQUENCE: 15

```
Met Ser Glu His Arg His Gly Pro Gly Glu His Gly His His His
1               5                   10                  15

Asp Asn His Leu Thr Asp Met Glu Ala Arg Val Lys Ala Leu Glu Thr
            20                  25                  30

Val Leu Thr Glu Lys Gly Leu Ile Asp Pro Ala Ala Ile Asp Ala Ile
            35                  40                  45

Val Asp Thr Tyr Glu Thr Lys Val Gly Pro Arg Asn Gly Ala Arg Val
    50                  55                  60

Val Ala Lys Ala Trp Ser Asp Pro Asp Phe Ala Asp Trp Leu Arg Arg
65                  70                  75                  80

Asp Ala Thr Ala Ala Ile Ala Ser Leu Gly Phe Thr Gly Arg Gln Gly
                85                  90                  95

Glu His Met Arg Ala Val Phe Asn Thr Ser Glu Thr His Asn Leu Ile
            100                 105                 110

Val Cys Thr Leu Cys Ser Cys Tyr Pro Trp Ala Val Leu Gly Leu Pro
            115                 120                 125

Pro Val Trp Tyr Lys Ala Pro Pro Tyr Arg Ser Arg Ala Val Ile Asp
    130                 135                 140

Pro Arg Gly Val Leu Ala Glu Phe Gly Leu Asn Leu Pro Ala Glu Lys
145                 150                 155                 160

Lys Ile Arg Val Trp Asp Ser Thr Ala Glu Leu Arg Tyr Leu Val Val
                165                 170                 175

Pro Glu Arg Pro Ala Ala Thr Asp Asp Leu Gly Glu Asp Ala Leu Ala
            180                 185                 190

Lys Leu Val Thr Arg Asp Ser Met Ile Gly Thr Gly Leu Ala Leu Ser
            195                 200                 205

Pro Glu Ala Phe Arg
    210
```

<210> SEQ ID NO 16
<211> LENGTH: 205
<212> TYPE: PRT
<213> ORGANISM: Geobacillus thermoglucosidasius Q6

<400> SEQUENCE: 16

```
Met Ser Val Gln Lys Val His His Asn Val Leu Pro Glu Lys Pro Ala
1               5                   10                  15

Gln Thr Arg Thr Lys Ala Leu Glu Ser Leu Leu Ile Glu Ser Gly Leu
            20                  25                  30

Val Ser Thr Asp Ala Leu Asp Ala Ile Ile Glu Ala Tyr Glu Asn Asp
            35                  40                  45

Ile Gly Pro Met Asn Gly Ala Lys Val Val Ala Lys Ala Trp Val Asp
    50                  55                  60

Pro Asp Tyr Lys Glu Arg Leu Leu Arg Asp Gly Thr Ser Ala Ile Ala
65                  70                  75                  80

Glu Leu Gly Phe Leu Gly Leu Gln Gly Glu His Met Val Val Val Glu
```

```
            85                  90                  95
Asn Thr Pro Lys Val His Asn Val Val Cys Thr Leu Cys Ser Cys
            100                 105                 110

Tyr Pro Trp Pro Val Leu Gly Leu Pro Pro Ser Trp Tyr Lys Ser Ala
            115                 120                 125

Ser Tyr Arg Ala Arg Ile Val Ser Glu Pro Arg Thr Val Leu Lys Glu
            130                 135                 140

Phe Gly Leu Glu Leu Asp Asp Val Glu Ile Arg Val Trp Asp Ser
145                 150                 155                 160

Ser Ala Glu Ile Arg Tyr Leu Val Leu Pro Glu Arg Pro Ala Gly Thr
                    165                 170                 175

Glu Gly Trp Ser Glu Glu Leu Ala Lys Leu Val Thr Arg Asp Ser
            180                 185                 190

Met Ile Gly Val Ala Lys Ile Lys Ser Pro Val Lys Lys
            195                 200                 205

<210> SEQ ID NO 17
<211> LENGTH: 205
<212> TYPE: PRT
<213> ORGANISM: Pseudonocardia thermophila JCM3095

<400> SEQUENCE: 17

Met Thr Glu Asn Ile Leu Arg Lys Ser Asp Glu Glu Ile Gln Lys Glu
1               5                   10                  15

Ile Thr Ala Arg Val Lys Ala Leu Glu Ser Met Leu Ile Glu Gln Gly
                20                  25                  30

Ile Leu Thr Thr Ser Met Ile Asp Arg Met Ala Glu Ile Tyr Glu Asn
            35                  40                  45

Glu Val Gly Pro His Leu Gly Ala Lys Val Val Lys Ala Trp Thr
    50                  55                  60

Asp Pro Glu Phe Lys Lys Arg Leu Leu Ala Asp Gly Thr Glu Ala Cys
65                  70                  75                  80

Lys Glu Leu Gly Ile Gly Gly Leu Gln Gly Glu Asp Met Met Trp Val
                85                  90                  95

Glu Asn Thr Asp Glu Val His His Val Val Cys Thr Leu Cys Ser
            100                 105                 110

Cys Tyr Pro Trp Pro Val Leu Gly Leu Pro Pro Asn Trp Phe Lys Glu
            115                 120                 125

Pro Gln Tyr Arg Ser Arg Val Val Arg Glu Pro Arg Gln Leu Leu Lys
            130                 135                 140

Glu Glu Phe Gly Phe Glu Val Pro Pro Ser Lys Glu Ile Lys Val Trp
145                 150                 155                 160

Asp Ser Ser Ser Glu Met Arg Phe Val Val Leu Pro Gln Arg Pro Ala
                    165                 170                 175

Gly Thr Asp Gly Trp Ser Glu Glu Leu Ala Thr Leu Val Thr Arg
            180                 185                 190

Glu Ser Met Ile Gly Val Glu Pro Ala Lys Ala Val Ala
            195                 200                 205

<210> SEQ ID NO 18
<211> LENGTH: 207
<212> TYPE: PRT
<213> ORGANISM: Rhodococcus rhodochrous Cr4

<400> SEQUENCE: 18

Met Thr Ala His Asn Pro Val Gln Gly Thr Phe Pro Arg Ser Asn Glu
```

```
 1               5                  10                  15
Glu Ile Ala Ala Arg Val Lys Ala Met Glu Ala Ile Leu Val Asp Lys
                20                  25                  30
Gly Leu Ile Ser Thr Asp Ala Ile Asp Tyr Met Ser Ser Val Tyr Glu
                35                  40                  45
Asn Glu Val Gly Pro Gln Leu Gly Ala Lys Ile Ala Ala His Ala Trp
    50                  55                  60
Val Asp Pro Glu Phe Lys Gln Arg Leu Leu Ala Asp Ala Thr Gly Ala
65                  70                  75                  80
Cys Lys Glu Met Gly Val Gly Gly Met Gln Gly Glu Glu Met Val Val
                85                  90                  95
Leu Glu Asn Thr Asp Thr Val Asn Asn Met Val Val Cys Thr Leu Cys
                100                 105                 110
Ser Cys Tyr Pro Trp Pro Val Leu Gly Leu Pro Pro Asn Trp Tyr Lys
                115                 120                 125
Tyr Pro Ala Tyr Arg Ala Arg Ala Ala Arg Asp Pro Arg Gly Val Met
        130                 135                 140
Ala Glu Phe Gly Tyr Thr Pro Ala Ser Asp Val Glu Ile Arg Val Trp
145                 150                 155                 160
Asp Ser Ser Ala Glu Leu Arg Tyr Trp Val Leu Pro Gln Arg Pro Ala
                165                 170                 175
Gly Thr Glu Asn Phe Thr Glu Glu Gln Leu Ala Ala Leu Val Thr Arg
                180                 185                 190
Asp Ser Leu Ile Gly Val Ser Val Pro Thr Ala Pro Asn Lys Ala
                195                 200                 205

<210> SEQ ID NO 19
<211> LENGTH: 210
<212> TYPE: PRT
<213> ORGANISM: Comamonas testosteroni

<400> SEQUENCE: 19

Met Gly Gln Ser His Thr His Asp His His Asp Gly Tyr Gln Ala
1               5                   10                  15
Pro Pro Glu Asp Ile Ala Leu Arg Val Lys Ala Leu Glu Ser Leu Leu
                20                  25                  30
Ile Glu Lys Gly Leu Val Asp Pro Ala Ala Met Asp Leu Val Val Gln
                35                  40                  45
Thr Tyr Glu His Lys Val Gly Pro Arg Asn Gly Ala Lys Val Val Ala
    50                  55                  60
Lys Ala Trp Val Asp Pro Ala Tyr Lys Ala Arg Leu Leu Ala Asp Gly
65                  70                  75                  80
Thr Ala Gly Ile Ala Glu Leu Gly Phe Ser Gly Val Gln Gly Glu Asp
                85                  90                  95
Met Val Ile Leu Glu Asn Thr Pro Ala Val His Asn Val Val Val Cys
                100                 105                 110
Thr Leu Cys Ser Cys Tyr Pro Trp Pro Thr Leu Gly Leu Pro Pro Ala
                115                 120                 125
Trp Tyr Lys Ala Pro Pro Tyr Arg Ser Arg Met Val Ser Asp Pro Arg
        130                 135                 140
Gly Val Leu Ala Glu Phe Gly Leu Val Ile Pro Ala Lys Glu Ile Arg
145                 150                 155                 160
Val Trp Asp Thr Thr Ala Glu Leu Arg Tyr Met Val Leu Pro Glu Arg
                165                 170                 175
```

Pro Ala Gly Thr Glu Ala Tyr Ser Glu Glu Gln Leu Ala Glu Leu Val
            180                 185                 190

Thr Arg Asp Ser Met Ile Gly Thr Gly Leu Pro Ile Gln Pro Thr Pro
        195                 200                 205

Ser His
    210

<210> SEQ ID NO 20
<211> LENGTH: 27
<212> TYPE: DNA
<213> ORGANISM: Artificial Sequence
<220> FEATURE:
<223> OTHER INFORMATION: alfa8G-F primer

<400> SEQUENCE: 20
aataagggca cggagtacga ggcacgt                                          27

<210> SEQ ID NO 21
<211> LENGTH: 27
<212> TYPE: DNA
<213> ORGANISM: Artificial Sequence
<220> FEATURE:
<223> OTHER INFORMATION: alfa8G-R primer

<400> SEQUENCE: 21
ctccgtgccc ttattgacgt gctcgct                                          27

<210> SEQ ID NO 22
<211> LENGTH: 27
<212> TYPE: DNA
<213> ORGANISM: Artificial Sequence
<220> FEATURE:
<223> OTHER INFORMATION: alfa8V-F primer

<400> SEQUENCE: 22
aataaggtca cggagtacga ggcacgt                                          27

<210> SEQ ID NO 23
<211> LENGTH: 27
<212> TYPE: DNA
<213> ORGANISM: Artificial Sequence
<220> FEATURE:
<223> OTHER INFORMATION: alfa8V-R primer

<400> SEQUENCE: 23
ctccgtgacc ttattgacgt gctcgct                                          27

<210> SEQ ID NO 24
<211> LENGTH: 27
<212> TYPE: DNA
<213> ORGANISM: Artificial Sequence
<220> FEATURE:
<223> OTHER INFORMATION: alfa88V-F primer

<400> SEQUENCE: 24
ccaaattgtc gcggtcttca acgactc                                          27

<210> SEQ ID NO 25
<211> LENGTH: 27
<212> TYPE: DNA
<213> ORGANISM: Artificial Sequence
<220> FEATURE:
<223> OTHER INFORMATION: alfa88V-R primer

<400> SEQUENCE: 25
gaccgcgaca atttggtgtg cctgctc                                              27

<210> SEQ ID NO 26
<211> LENGTH: 27
<212> TYPE: DNA
<213> ORGANISM: Artificial Sequence
<220> FEATURE:
<223> OTHER INFORMATION: alfa153I-F primer

<400> SEQUENCE: 26
gtcaggatct gggacagcag ctccgaa                                              27

<210> SEQ ID NO 27
<211> LENGTH: 27
<212> TYPE: DNA
<213> ORGANISM: Artificial Sequence
<220> FEATURE:
<223> OTHER INFORMATION: alfa153I-R primer

<400> SEQUENCE: 27
gtcccagatc ctgacctcca cctcatc                                              27

<210> SEQ ID NO 28
<211> LENGTH: 27
<212> TYPE: DNA
<213> ORGANISM: Artificial Sequence
<220> FEATURE:
<223> OTHER INFORMATION: alfa153L-F primer

<400> SEQUENCE: 28
gtcaggctct gggacagcag ctccgaa                                              27

<210> SEQ ID NO 29
<211> LENGTH: 27
<212> TYPE: DNA
<213> ORGANISM: Artificial Sequence
<220> FEATURE:
<223> OTHER INFORMATION: alfa153L-R primer

<400> SEQUENCE: 29
gtcagggagt gggacagcag ctccgaa                                              27

<210> SEQ ID NO 30
<211> LENGTH: 27
<212> TYPE: DNA
<213> ORGANISM: Artificial Sequence
<220> FEATURE:
<223> OTHER INFORMATION: alfa153M-F primer

<400> SEQUENCE: 30
gtcaggatgt gggacagcag ctccgaa                                              27

<210> SEQ ID NO 31
<211> LENGTH: 27
<212> TYPE: DNA
<213> ORGANISM: Artificial Sequence
<220> FEATURE:
<223> OTHER INFORMATION: alfa153M-R primer

<400> SEQUENCE: 31
gtcaggcatt gggacagcag ctccgaa                                              27

<210> SEQ ID NO 32
<211> LENGTH: 27
<212> TYPE: DNA
<213> ORGANISM: Artificial Sequence

```
<220> FEATURE:
<223> OTHER INFORMATION: alfa153T-F primer

<400> SEQUENCE: 32
gtcaggacct gggacagcag ctccgaa                                      27

<210> SEQ ID NO 33
<211> LENGTH: 27
<212> TYPE: DNA
<213> ORGANISM: Artificial Sequence
<220> FEATURE:
<223> OTHER INFORMATION: alfa153T-R primer

<400> SEQUENCE: 33
gtcaggggtt gggacagcag ctccgaa                                      27

<210> SEQ ID NO 34
<211> LENGTH: 27
<212> TYPE: DNA
<213> ORGANISM: Artificial Sequence
<220> FEATURE:
<223> OTHER INFORMATION: alfa154L-F primer

<400> SEQUENCE: 34
agggttctcg acagcagctc cgaaatc                                      27

<210> SEQ ID NO 35
<211> LENGTH: 27
<212> TYPE: DNA
<213> ORGANISM: Artificial Sequence
<220> FEATURE:
<223> OTHER INFORMATION: alfa154L-R primer

<400> SEQUENCE: 35
gctgtcgaga accctgacct ccacctc                                      27

<210> SEQ ID NO 36
<211> LENGTH: 27
<212> TYPE: DNA
<213> ORGANISM: Artificial Sequence
<220> FEATURE:
<223> OTHER INFORMATION: a153I?/Ea154L-F primer

<400> SEQUENCE: 36
gtcaggatcc tcgacagcag ctccgaa                                      27

<210> SEQ ID NO 37
<211> LENGTH: 27
<212> TYPE: DNA
<213> ORGANISM: Artificial Sequence
<220> FEATURE:
<223> OTHER INFORMATION: a153I/a154L-R primer

<400> SEQUENCE: 37
gctgtcgagg atcctgacct ccacctc                                      27

<210> SEQ ID NO 38
<211> LENGTH: 27
<212> TYPE: DNA
<213> ORGANISM: Artificial Sequence
<220> FEATURE:
<223> OTHER INFORMATION: a153L/a154L-F primer

<400> SEQUENCE: 38
gtcaggctcc tcgacagcag ctccgaa                                      27
```

<210> SEQ ID NO 39
<211> LENGTH: 27
<212> TYPE: DNA
<213> ORGANISM: Artificial Sequence
<220> FEATURE:
<223> OTHER INFORMATION: a153L/a154L-R primer

<400> SEQUENCE: 39
gctgtcgagg agcctgacct ccacctc					27

<210> SEQ ID NO 40
<211> LENGTH: 27
<212> TYPE: DNA
<213> ORGANISM: Artificial Sequence
<220> FEATURE:
<223> OTHER INFORMATION: a153M/a154L-F primer

<400> SEQUENCE: 40
gtcaggatgc tcgacagcag ctccgaa					27

<210> SEQ ID NO 41
<211> LENGTH: 27
<212> TYPE: DNA
<213> ORGANISM: Artificial Sequence
<220> FEATURE:
<223> OTHER INFORMATION: a153M/a154L-R

<400> SEQUENCE: 41
gctgtcgagc atcctgacct ccacctc					27

<210> SEQ ID NO 42
<211> LENGTH: 27
<212> TYPE: DNA
<213> ORGANISM: Artificial Sequence
<220> FEATURE:
<223> OTHER INFORMATION: a153T/a154L-F primer

<400> SEQUENCE: 42
gtcaggaccc tcgacagcag ctccgaa					27

<210> SEQ ID NO 43
<211> LENGTH: 27
<212> TYPE: DNA
<213> ORGANISM: Artificial Sequence
<220> FEATURE:
<223> OTHER INFORMATION: a153T/a154L-R primer

<400> SEQUENCE: 43
gctgtcgagg agcctgacct ccacctc					27

<210> SEQ ID NO 44
<211> LENGTH: 1315
<212> TYPE: DNA
<213> ORGANISM: Nocardia

<400> SEQUENCE: 44
atggatggta tccacgacac aggcggcatg accggatacg accggtccc ctatcagaag			60 gacgagccct tcttccacta cgagtgggag ggtcggaccc tgtcgattct gacctggatg			120 catctcaagg gcatgtcgtg gtgggacaag tcgcggttct tccgggagtc gatggggaac			180 gaaaactacg tcaacgagat tgcaactcg tactacaccc actggctgag tgcggcagaa			240 cgtatcctcg tcgccgacaa gatcatcacc gaagaagagc gaaagcaccg tgtgcaggag			300 atcctcgagg gtcggtacac ggacaggaac ccgtcgcgga gttcgatcc ggccgagatc			360

```
gagaaggcga tcgaacggct tcacgagccc cactccctag cacttccagg agcggagccg    420
agtttctccc tcggtgacaa ggtcaaagtg aagaatatga acccgctggg acacacacgg    480
tgcccgaaat atgtgcggaa caagatcggg gaaatcgtca cctcccacgg ctgccagatc    540
tatcccgaga gcagctccgc cggcctcggc gacgatcccc gcccgctcta cacggtcgcg    600
ttttccgccc aggaactgtg gggcgacgac ggaaacggga agacgtagt gtgcgtcgat    660
ctctgggaac cgtacctgat ctctgcgtga aggaatacg atagtgagcg agcacgtcaa    720
taagtacacg gagtacgagg cacgtaccaa ggcaatcgaa actttgctgt acgagcgagg    780
gctcatcacg cccgccgcgg tcgaccgagt cgtttcgtac tacgagaacg agatcggccc    840
gatgggcggt gccaaggtcg tggcgaagtc ctgggtggac cctgagtacc gcaagtggct    900
cgaagaggac gcgacggccg cgatggcgtc attgggctat gccggtgagc aggcacacca    960
aatttcggcg gtcttcaacg actcccaaac gcatcacgtg gtggtgtgca ctctgtgttc   1020
gtgctatccg tggccggtgc ttggtctccc gcccgcctgg tacaagagca tggagtaccg   1080
gtcccgagtg gtagcggacc ctcgtggagt gctcaagcgc gatttcggtt tcgacatccc   1140
cgatgaggtg gaggtcaggg tttgggacag cagctccgaa atccgctaca tcgtcatccc   1200
ggaacggccg gccggcaccg acggttggtc cgaggacgag ctggcgaagc tggtgagccg   1260
ggactcgatg atcggtgtca gtaatgcgct cacaccccag gaagtgatcg tatga        1315

<210> SEQ ID NO 45
<211> LENGTH: 1315
<212> TYPE: DNA
<213> ORGANISM: Rhodococcus pyridinovorans S85-2

<400> SEQUENCE: 45
atggatggta tccacgacac aggcggcatg accggatacg gaccggtccc ctatcagaag     60
gacgagccct tcttccacta cgagtgggag ggtcggaccc tgtcgattct gacttggatg    120
catctcaagg gcatatcgtg gtgggacaag tcgcggttct ccgggagtc gatggggaac    180
gaaaactacg tcaacgagat cgcaactcg tactacaccc actggctgag tgcggcagaa    240
cgtatcctcg tcgccgacaa gatcatcacc gaagaagagc gaaagcaccg tgtgcaagag    300
atccttgagg tcggtacac ggacaggaag ccgtcgcgga agttcgatcc ggcccagatc    360
gagaaggcga tcgaacggct tcacgagccc cactccctag cacttccagg agcggagccg    420
agtttctctc tcggtgacaa gatcaaagtg aagagtatga acccgctggg acacacacgg    480
tgcccgaaat atgtgcggaa caagatcggg gaaatcgtca cctaccacgg ctgccagatc    540
tatcccgaga gcagctccgc cggcctcggc gacgatcctc gcccgctcta cacggtcgcg    600
ttttccgccc aggaactgtg gggcgacgac ggaaacggga agacgtagt gtgcgtcgat    660
ctctgggaac cgtacctgat ctctgcgtga aggaatacg atagtgagcg agcacgtcaa    720
taagtacacg gagtacgagg cacgtaccaa ggcgatcgaa accttgctgt acgagcgagg    780
gctcatcacg cccgccgcgg tcgaccgagt cgtttcgtac tacgagaacg agatcggccc    840
gatgggcggt gccaaggtcg tggccaagtc ctgggtggac cctgagtacc gcaagtggct    900
cgaagaggac gcgacggccg cgatggcgtc attgggctat gccggtgagc aggcacacca    960
aatttcggcg gtcttcaacg actcccaaac gcatcacgtg gtggtgtgca ctctgtgttc   1020
gtgctatccg tggccggtgc ttggtctccc gcccgcctgg tacaagagca tggagtaccg   1080
gtcccgagtg gtagcggacc ctcgtggagt gctcaagcgc gatttcggtt tcgacatccc   1140
```
cgatgaggtg gaggtcaggg tttgggacag cagctccgaa atccgctaca tcgtcatccc   1200
ggaacggccg gccggcaccg acggttggtc cgaggaggag ctgacgaagc tggtgagccg   1260
ggactcgatg atcggtgtca gtaatgcgct cacaccgcag gaagtgatcg tatga       1315

<210> SEQ ID NO 46
<211> LENGTH: 12
<212> TYPE: PRT
<213> ORGANISM: Artificial Sequence
<220> FEATURE:
<223> OTHER INFORMATION: synthetic peptide sequence corresponding to
      positions 8 to 19 of the amino acid sequence of the alpha subunit
      of a nitrile hydratase
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid

<400> SEQUENCE: 46

Xaa Xaa Xaa Xaa Xaa Xaa Arg Xaa Lys Ala Xaa Glu
1               5                   10

<210> SEQ ID NO 47
<211> LENGTH: 18
<212> TYPE: PRT
<213> ORGANISM: Artificial Sequence
<220> FEATURE:
<223> OTHER INFORMATION: synthetic peptide sequence corresponding to
      positions 88 to 105 of the amino acid sequence of the alpha
      subunit of a nitrile hydratase
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(14)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 47

Xaa Xaa Xaa Xaa Asn Xaa Xaa Xaa Xaa Xaa Xaa Xaa Xaa Xaa Cys Xaa
1               5                   10                  15

Leu Cys

<210> SEQ ID NO 48
<211> LENGTH: 12
<212> TYPE: PRT
<213> ORGANISM: Artificial Sequence
<220> FEATURE:
<223> OTHER INFORMATION: synthetic peptide sequence corresponding to
      positions 153 to 164 of the amino acid sequence of the alpha
      subunit of a nitrile hydratase
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 48

Xaa Trp Asp Ser Xaa Xaa Glu Xaa Arg Xaa Xaa Val
1               5                   10

<210> SEQ ID NO 49
<211> LENGTH: 12
<212> TYPE: PRT
<213> ORGANISM: Artificial Sequence
<220> FEATURE:
<223> OTHER INFORMATION: synthetic peptide sequence corresponding to
      positions 153 to 164 of the amino acid sequence of the alpha
      subunit of a nitrile hydratase
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid

<400> SEQUENCE: 49

Val Xaa Asp Ser Xaa Xaa Glu Xaa Arg Xaa Xaa Val
1               5                   10

<210> SEQ ID NO 50
<211> LENGTH: 203
<212> TYPE: PRT
<213> ORGANISM: Artificial Sequence
<220> FEATURE:
<223> OTHER INFORMATION: synthetic peptide of alpha subunit of a nitrile
      hydratase
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (88)..(91)
<223> OTHER INFORMATION: Xaa can be any naturally occurring amino acid
<220> FEATURE:
<221> NAME/KEY: misc_feature
<222> LOCATION: (93)..(101)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature

```
<222> LOCATION: (153)..(154)
<223> OTHER INFORMATION: Xaa can be any naturally occurring amino acid
<220> FEATURE:
<221> NAME/KEY: misc_feature
<222> LOCATION: (157)..(158)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (162)..(163)
<223> OTHER INFORMATION: Xaa can be any naturally occurring amino acid

<400> SEQUENCE: 50

Met Ser Glu His Val Asn Lys Xaa Xaa Xaa Xaa Xaa Xaa Arg Xaa Lys
1               5                   10                  15

Ala Xaa Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Xaa Xaa Xaa Xaa Asn Xaa Xaa Xaa Xaa
                85                  90                  95

Xaa Xaa Xaa Xaa Xaa Cys Xaa Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Xaa Xaa Asp Ser Xaa Xaa Glu Xaa
145                 150                 155                 160

Arg Xaa Xaa Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200

<210> SEQ ID NO 51
<211> LENGTH: 33
<212> TYPE: DNA
<213> ORGANISM: Artificial Sequence
<220> FEATURE:
<223> OTHER INFORMATION: NH-F primer

<400> SEQUENCE: 51
gaagtgatcg tatgagtgaa gacacactca ctg                                    33

<210> SEQ ID NO 52
<211> LENGTH: 33
<212> TYPE: DNA
<213> ORGANISM: Artificial Sequence
<220> FEATURE:
<223> OTHER INFORMATION: NH-R primer

<400> SEQUENCE: 52
gtggatacca tccatttcct cattcctttc atc                                    33
```

```
<210> SEQ ID NO 53
<211> LENGTH: 27
<212> TYPE: DNA
<213> ORGANISM: Artificial Sequence
<220> FEATURE:
<223> OTHER INFORMATION: a88T-F primer

<400> SEQUENCE: 53
ccaaattacc gcggtcttca acgactc                                              27

<210> SEQ ID NO 54
<211> LENGTH: 27
<212> TYPE: DNA
<213> ORGANISM: Artificial Sequence
<220> FEATURE:
<223> OTHER INFORMATION: a88T-R primer

<400> SEQUENCE: 54
gaccgcggta atttggtgtg cctgctc                                              27

<210> SEQ ID NO 55
<211> LENGTH: 6
<212> TYPE: PRT
<213> ORGANISM: Rhodococcus rhodochrous
<220> FEATURE:
<221> NAME/KEY: MISC_FEATURE
<222> LOCATION: (2)..(2)
<223> OTHER INFORMATION: Xaa stands for Ser or Thr

<400> SEQUENCE: 55

Cys Xaa Leu Cys Ser Cys
1               5

<210> SEQ ID NO 56
<211> LENGTH: 6
<212> TYPE: PRT
<213> ORGANISM: Rhodococcus rhodochrous

<400> SEQUENCE: 56

Cys Ser Leu Cys Ser Cys
1               5

<210> SEQ ID NO 57
<211> LENGTH: 6
<212> TYPE: PRT
<213> ORGANISM: Rhodococcus rhodochrous

<400> SEQUENCE: 57

Cys Thr Leu Cys Ser Cys
1               5
```

The invention claimed is:

1. An isolated modified nitrile hydratase comprising an α subunit, wherein the α subunit comprises at least one amino acid sequence selected from the group consisting of SEQ ID NO: 46, 47, 48, and 49,
wherein:
(a) SEQ ID NO: 46: $X_1X_2X_3X_4X_5X_6RX_7KAX_8E$,
wherein
$X_1$ is an amino acid other than tyrosine; $X_2$, $X_3$, $X_5$, $X_6$, $X_7$ and $X_8$ each independently are any amino acid residue; and $X_4$ is tyrosine, and
SEQ ID NO: 46 corresponds to amino acids in positions from 8 to 19 of SEQ ID NO:50;

(b) SEQ ID NO: 47: $X_9X_{10}X_{11}X_{12}NX_{13}X_{14}X_{15}X_{16}X_{17}X_{18}X_{19}X_{20}X_{21}CX_{22}LC$,
wherein
$X_9$ is an amino acid other than serine; $X_{10}$, $X_{11}$, $X_{12}$, $X_{13}$, $X_{14}$, $X_{15}$, $X_{16}$, $X_{17}$, $X_{19}$, $X_{20}$, $X_{21}$ and $X_{22}$ each independently are any amino acid residue; and $X_{18}$ is histidine, and
SEQ ID NO: 47 corresponds to amino acids in positions from 88 to 105 of SEQ ID NO:50;

(c) SEQ ID NO: 48: $X_{23}WDSX_{25}X_{26}EX_{27}RX_{28}X_{29}V$,
wherein
$X_{23}$ indicates an amino acid other than valine; $X_{25}$, $X_{27}$, $X_{28}$ and $X_{29}$ each independently are any amino acid residue; and $X_{26}$ is serine; and SEQ ID NO: 48 corresponds to amino acids in positions from 153 to 165 of SEQ ID NO:50;

(d) SEQ ID NO: 49: $VX_{24}DSX_{25}X_{26}EX_{27}RX_{28}X_{29}V$, wherein $X_{24}$ is an amino acid other than tryptophan; $X_{25}$, $X_{27}$, $X_{28}$ and $X_{29}$ each independently are any amino acid residue; and $X_{26}$ is serine; and SEQ ID NO: 49 corresponds to amino acids in positions from 153 to 165 of SEQ ID NO:50.

2. The isolated modified nitrile hydratase of claim 1 comprising an α subunit in which from 1 to 10 amino-acid residues are deleted, substituted, or added at positions other than X1, X9, X23, and X24 in the amino acid sequence of SEQ ID NO: 50 and has an enhanced resistance to amide compounds.

3. The nitrile hydratase according to claim 1, comprising at least the amino acid sequence of SEQ ID NO: 47 in the α subunit:

(b) SEQ ID NO: 47: $X_9X_{10}X_{11}X_{12}NX_{13}X_{14}X_{15}X_{16}X_{17}X_{18}X_{19}X_{20}X_{21}CX_{22}LC$, wherein $X_9$ is an amino acid other than serine; $X_{10}$, $X_{11}$, $X_{12}$, $X_{13}$, $X_{14}$, $X_{15}$, $X_{16}$, $X_{17}$, $X_{19}$ and $X_{20}$ each independently are any amino acid residue; $X_{18}$ is histidine; $X_{21}$ is valine; and $X_{22}$ is threonine.

4. The nitrile hydratase according to claim 1, comprising at least one amino acid sequence selected from the group consisting of SEQ ID NO: 46, 47, 48, and 49:

(a) SEQ ID NO: 46: $X_1X_2X_3X_4X_5X_6RX_7KAX_8E$, wherein $X_1$ is glycine or valine; $X_2$, $X_3$, $X_5$, $X_6$, $X_7$ and $X_8$ each independently are any amino acid residue; and $X_4$ is tyrosine;

(b) SEQ ID NO: 47: $X_9X_{10}X_{11}X_{12}NX_{13}X_{14}X_{15}X_{16}X_{17}X_{18}X_{19}X_{20}X_{21}CX_{22}LC$, wherein $X_9$ is valine or threonine; $X_{10}$, $X_{11}$, $X_{12}$, $X_{13}$, $X_{14}$, $X_{15}$, $X_{16}$, $X_{17}$, $X_{19}$ and $X_{20}$ each independently are any amino acid residue; $X_{18}$ is histidine; $X_{21}$ is valine; and $X_{22}$ is threonine;

(c) SEQ ID NO: 48: $X_{23}WDSX_{25}X_{26}EX_{27}RX_{28}X_{29}V$, wherein $X_{23}$ is selected from the group consisting of isoleucine, leucine, methionine, and threonine; $X_{25}$, $X_{27}$, $X_{28}$ and $X_{29}$ each independently are any amino acid residue; and $X_{26}$ is serine; and (d) SEQ ID NO: 49: $VX_{24}DSX_{25}X_{26}EX_{27}RX_{28}X_{29}V$, wherein $X_{24}$ is leucine $X_{25}$, $X_{27}$, $X_{28}$ and $X_{29}$ each independently are any amino acid residue; and $X_{26}$ is serine.

5. The nitrile hydratase according to claim 1, wherein in SEQ ID NO: 46, $X_2$ is threonine, $X_3$ is glutamic acid, $X_5$ is glutamic acid, $X_6$ is alanine, $X_7$ is threonine, and $X_8$ is isoleucine, in SEQ ID NO: 47, $X_{10}$ is alanine, $X_{11}$ is valine, $X_{12}$ is phenylalanine, $X_{13}$ is aspartic acid, $X_{14}$ is serine, $X_{15}$ is glutamine, $X_{16}$ is threonine, $X_{17}$ is histidine, $X_{19}$ is valine and $X_{20}$ is valine, and in SEQ ID NO: 48 and 49, $X_{25}$ is serine, $X_{27}$ is isoleucine, $X_{28}$ is tyrosine and $X_{29}$ is isoleucine.

6. The isolated modified nitrile hydratase of claim 1, comprising at least one amino acid mutation in SEQ ID NO:50 selected from the group consisting of (i), (ii), (iii), and (iv):

(i) $X_1$ is glycine or valine, (ii) $X_9$ is valine or threonine, (iii) $X_{23}$ is an amino acid selected from the group consisting of isoleucine, leucine, methionine, and threonine, and (iv) $X_{24}$ is leucine.

7. The nitrile hydratase according claim 6, wherein $X_2$ is threonine, $X_3$ is glutamic acid, $X_4$ is tyrosine, $X_5$ is glutamic acid, $X_6$ is alanine, $X_7$ is threonine, $X_8$ is isoleucine, $X_{10}$ is alanine, $X_{11}$ is valine, $X_{12}$ is phenylalanine, $X_{13}$ is aspartic acid, $X_{14}$ is serine, $X_{15}$ is glutamine, $X_{16}$ is threonine, $X_{17}$ is histidine, $X_{18}$ is histidine, $X_{19}$ is valine, $X_{20}$ is valine, $X_{25}$ is serine, $X_{26}$ is serine, $X_{27}$ is isoleucine, $X_{28}$ is tyrosine, and $X_{29}$ is isoleucine.

8. The nitrile hydratase according to claim 1, wherein the nitrile hydratase is from *Rhodococcus* bacterium or *Nocardia* bacterium that has been modified so that its α subunit comprises the amino acid sequence of SEQ ID NO:50.

9. An isolated polynucleotide encoding the nitrile hydratase of claim 1, or a polynucleotide which hybridizes under stringent conditions of a salt concentration of 300 to 2000 mM and a temperature of 40 to 75° C., with a polynucleotide having a polynucleotide sequence complementary to the the polynucleotide encoding the nitrile hydratase and encodes a protein having a nitrile hydratase activity with enhanced resistance to amide compounds under high temperatures.

10. A recombinant vector comprising the isolated polynucleotide according to claim 9.

11. An isolated transformed host cell comprising the recombinant vector according to claim 10.

12. A method for producing a nitrile hydratase, the method comprising culturing the isolated transformed host cell according to claim 11 and collecting the nitrile hydratase from the obtained culture.

13. A method for producing an amide compound, the method comprising bringing a nitrile compound into contact with the nitrile hydratase according to claim 1.

* * * * *